(12) United States Patent
Nagase et al.

(10) Patent No.: US 6,316,461 B1
(45) Date of Patent: Nov. 13, 2001

(54) ANTIPRURITIC

(75) Inventors: Hiroshi Nagase; Jun Utsumi; Takashi Endoh; Toshiaki Tanaka; Junzo Kamei; Kuniaki Kawamura, all of Kanagawa (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 09/615,540

(22) Filed: Jul. 13, 2000

Related U.S. Application Data

(62) Division of application No. 09/117,052, filed on Aug. 24, 1998, now Pat. No. 6,174,891.

(30) Foreign Application Priority Data

Nov. 25, 1996 (JP) ..................................... 8-313476

(51) Int. Cl.[7] ...................... A61K 31/485; C07D 221/28; C07D 489/100
(52) U.S. Cl. .............................. 514/282; 546/44; 546/45; 546/46
(58) Field of Search .............................. 514/282; 546/44, 546/45, 46

(56) References Cited

U.S. PATENT DOCUMENTS

| | | |
|---|---|---|
| 5,739,145 | 4/1998 | Nagase et al. . |
| 5,760,023 | 6/1998 | Farrar et al. . |
| 5,869,521 | 2/1999 | Farrar et al. . |

FOREIGN PATENT DOCUMENTS

WO 95/21843   8/1995  (WO) .

OTHER PUBLICATIONS

Cowan, Alan, and Gmereck, Debra E., "In–vivo studies on kappa opioid receptors", TIPS, Feb. 1986, pp. 69–72.

DeHaven–Hudkins, D. L. et al, "Opioid Agonist Properties of Two Oxime Derivatives of Naltrexone, NPC 831 and NPC 836", Pharmacology Biochemistry and Behavior, vol. 44, pp. 45–50, 1993.

Gmerek, Debra E., and Cowan, Alan, "An Animal Model for Preclinical Screening of Systemic Antipruritic Agents", Journal of Pharmacological Methods 10, 107–112 (1983).

*Primary Examiner*—Charanjit S. Aulakh
(74) *Attorney, Agent, or Firm*—Schnader Harrison Segal & Lewis LLP

(57) ABSTRACT

This invention provides an antipruritc comprising an opiate κ receptor agonist as an effective component, a new morphinan quaternary ammonium salt derivative and a new morphinan-N-oxide derivative which are useful in treating pruritus complicated with some diseases.

15 Claims, 1 Drawing Sheet

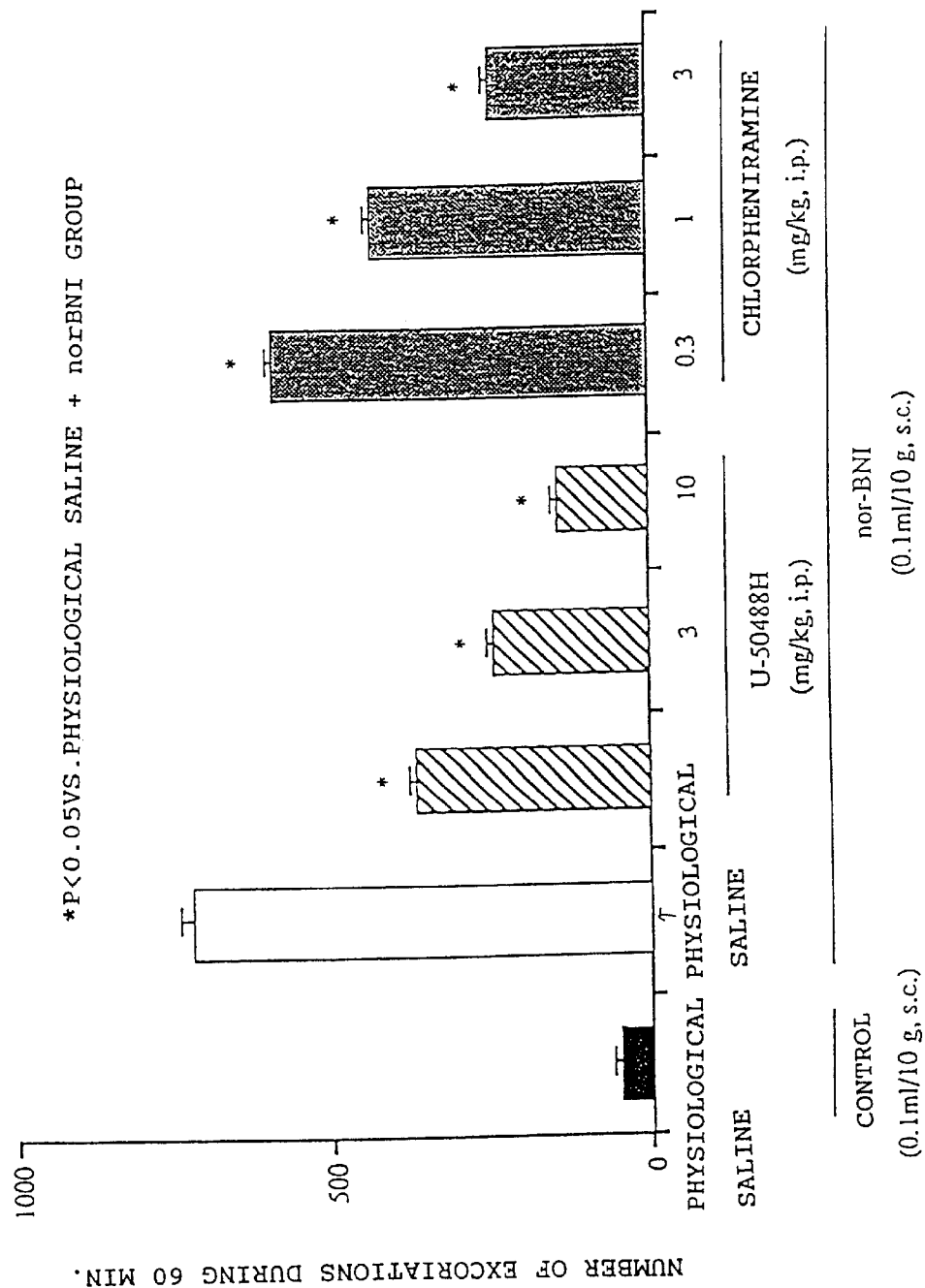
FIG. 1 ANTIPRURITIC EFFECT OF κ RECEPTOR AGONIST U-50488H ON κ RECEPTOR ANTAGONIST nor-BNI-INDUCED EXCORIATING BEHAVIOUR

ANTIPRURITIC

RELATED APPLICATIONS

This is a division out of U.S. application Ser. No. 09/117,052, filed Aug. 24, 1998 from which U.S. Pat. No. 6,174,891 was granted on Jan. 16, 2001. Priority is claimed of Japanese Application No. 08/313,476 filed Nov. 25, 1996, under 35 U.S.C. §119.

TECHNICAL FIELD

The present invention relates to an opiate κ receptor agonist and an antipruritic comprising it which are useful for the treatment of pruritus associated with various diseases.

BACKGROUND ART

Pruritus is an indication that is peculiar to skin, and is observed in a variety of dermatoses with inflammation. Pruritus may be provoked by some internal diseases (malignant tumors, diabetes mellitus, hepatic diseases, renal failure, hemodialysis, gout, thyroid diseases, hemopathy, and iron deficiency), pregnancy, and vermination. In some cases, drugs and psychogenic causes may also provoke pruritus.

Since pruritus is a subjective sensation, it is difficult to evaluate it quantitatively and objectively. The mechanism that induces pruritus has not yet been completely clarified.

Now, among the stimulants that are known to induce pruritus included are histamine, substance P, bradykinin, proteinases, prostaglandins, and opiate peptides. It is considered that pruritus is provoked by reaction of these pruritic stimulants to multistimuli-reacting nerve terminals existing at the border area between the epidermis and dermis (pruritic receptors), and by transfer of the resulting impulse to tractus spinothalamicus, thalamus, and cortex cerebri in that order ("The approach to the therapy for pruritus cutaneous", by Yoshiki Miyaji, p.22, 1996, Sentan Igakusya).

Pruritus is a symptom in which patients experience significant discomfort, and in severe cases may cause significant disturbance of normal life. In the therapy for pruritus, primarily the treatment of dermatitis or an underlying disease that induces pruritus is necessary, and particularly in cases of dermatoses, simultaneous therapy for pruritus itself is necessary, because scratching by a patient causes aggravation of symptoms.

Scratching is the most exacerbating factor of dermatitis, because scratching injures the skin resulting in defect of barrier function, and erosion by physical or chemical stimuli and bacterial infection may easily occur. Also, since the epidermis becomes thin and fragile and nerves are sensitized, pruritus readily occurs. As a result, a vicious cycle of repeated scratching begins.

For example, although the period of scratching resulting from pruritus during sleep is only 0.1% in healthy cases, the average period of scratching by patients with severe atopic dermatitis amounts to 24%. If an average period of sleep is assumed to be 8 hours, the period of scratching will reach about 2 hours. It is clear that the scratching during sleep exacerbates atopic dermatitis and becomes a factor in the occurrence of atpoic exanthema ("NIKKEI MEDICAL", Jul. 10, 1996, p13).

Thus the therapy for pruritus itself may be a radical treatment, particularly in cases of dermatosis with significant pruritus.

Examples of dermatoses generally subjected to therapy for such pruritus include atopic dermatitis, nervous dermatitis, contact dermatitis, seborrheic dermatitis, autosensitization dermatitis, caterpillar dermatitis, asteatosis, senile pruritus cutaneuos, insect sting, photosensitive dermatosis, urticaria, prurigo, herpes, impetigo, eczema, tinea, lichen, psoriasis, scabies, and acne vulgaris; and examples of visceral diseases complicated with pruritus and being particular problems include malignant tumors, diabetes mellitus, hepatic diseases, renal failure, hemodialysis, and pregnancy.

Examples of drugs generally used for therapy for such pruritus include oral drugs, e.g. topical, and antiallergic drugs; and topical preparations, e.g. antihistamines, adrenocortical steroid dermatologic preparations, nonsteroidal anti-inflammatory drugs, camphor, menthol, phenol, salicylic acid, tar, crotamiton, capsaicin, and humectants (urea, Hirudoid, and petrolatum). However, oral drugs have some problems, e.g. a long lag time before presenting effects, and adverse events such as suppressive effects on the central nervous system (drowsiness and fatigue) and impairment of the gastrointestinal system. Topical preparations also have some problems, e.g. insufficient antipruritic effect, while topical steroids particularly cause some problems of adverse events such as decreased adrenocortical function caused by protracted administration and the rebound phenomenon.

With regard to the relationship between opiates and pruritus, it has been clear that opiates have function not only as analgesics but also as chemical mediators of pruritus. It was first reported that endogenous opiate peptides such as β-endorphin and enkephalin induced pruritus (B. Fjeller Acta, Dermato-Venereol., 61 (suppl. 97), 1-34, 1981). It has been shown that morphine or opiate compounds induced pruritus as an adverse event when administered epidurally or intrathecally (J. H. Jaffe and W. R. Martin, Goodman and Gilman's Pharmacological Basis of Theraputics, Macmillan, New York, 1985). On the other hand, it has been also shown that pruritus which induced by morphine administered intrathecally was suppressed by naloxone, a morphine antagonist (J. Bernstein et al., J. Invest. Dermatol., 78, 82–83, 1982), and severe pruritus induced by increasing concentration of endogenous opiate peptides in cases of cholestasia with hepathopathy was suppressed by nalmefene (J. R. Thornton and M. S. Losowsky, Br. Med. J., 297, 1501–1504, 1988). Generally, opiate agonists induce pruritus, whereas opiate antagonists are antipruritic. Recently, it has become evident that the serum concentration of β-endorphin in children with atopic dermatitis is significantly higher than that of healthy children. And it was reported that opiate antagonists were effective in pruritus induced by atopic dermatitis (S. Georgala et al., J. Dermatol. Sci., 8, 125–128, 1994).

Thus, it has been generally recognized that opiate agonists induce pruritus and opiate antagonists have a possibility as antipruritic. However, opiate antagonists do not have a practical use as an antipruritic at the present stage.

An object of this invention is to provide an opiate κ receptor agonist and an antipruritic comprising it that solves the above problems and which has a significantly prompt and potent antipruritic activity.

DISCLOSURE OF INVENTION

The present invention provides an opiate κ receptor agonist and an antipruritic comprising it as an effective component.

BRIEF DESCRIPTION OF THE DRAWINGS

FIG. 1 shows the results of Example 11.

BEST MODE FOR CARRYING OUT THE INVENTION

It is known that there are $\mu$, $\delta$, and $\kappa$ opiate receptors, and endogenous opiate peptides each selectively stimulating corresponding receptors have been discovered. In other words, β-endorphin and enkephalin are identified as $\mu$, and $\delta$ receptor agonists, respectively, and dynorphin has been identified as an endogenous opiate peptide acting as a specific $\kappa$ receptor agonist. The effect of action of $\kappa$ receptor agonists including dynorphin on pruritus has not been clear, this invention, however, makes it clear for the first time.

Although the $\kappa$ receptor agonists of this invention may not have any chemical structural specificity regarding agonistic action on opiate $\kappa$ receptors, the agonists preferably have higher specificity for $\kappa$ receptors than $\mu$, and $\delta$ receptors. More particularly, morphinan derivatives or their pharmacologically acceptable salts with an added acid having an opiate $\kappa$ receptor agonistic activity are exemplified. Among these compounds are opiate $\kappa$ receptor agonists or their pharmacologically acceptable salt with an added acid represented by the general formula (I)

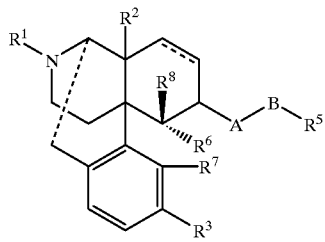

(I)

wherein ═══ is a double bond, or a single bond; $R^1$ is alkyl having 1 to 5 carbon atoms, cycloalkylalkyl having 4 to 7 carbon atoms, cycloalkenylalkyl having 5 to 7 carbon atoms, aryl having 6 to 12 carbon atoms, aralkyl having 7 to 13 carbon atoms, alkenyl having 4 to 7 carbon atoms, allyl, furan-2-ylalkyl having 1 to 5 carbon atoms, or thiophene-2-ylalkyl having 1 to 5 carbon atoms; $R^2$ is hydrogen, hydroxy, nitro, alkanoyloxy having 1 to 5 carbon atoms, alkoxy having 1 to 5 carbon atoms, alkyl having 1 to 5 carbon atoms, or —$NR^9R^{10}$; $R^9$ is hydrogen or alkyl having 1 to 5 carbon atoms; $R^{10}$ is hydrogen, alkyl having 1 to 5 carbon atoms, or —C(═O)—$R^{11}$; $R^{11}$ is hydrogen, phenyl, or alkyl having 1 to 5 carbon atoms; $R^3$ is hydrogen, hydroxy, alkanoyloxy having 1 to 5 carbon atoms, or alkoxy having 1 to 5 carbon atoms; A is —XC(═Y)—, —XC(═Y)Z—, —X—, or —$XSO_2$— (wherein X, Y, and Z are $NR^4$, S, or O independently; and $R^4$ is hydrogen, a straight or branched alkyl having 1 to 5 carbon atoms, or aryl having 6 to 12 carbon atoms; and in the formula $R^4$ may be the same or different); B is a valence bond, a straight or branched alkylene having 1 to 14 carbon atoms (wherein the alkylene may have at least one substituent selected from the group consisting of alkoxy having 1 to 5 carbon atoms, alkanoyloxy having 1 to 5 carbon atoms, hydroxy, fluorine, chlorine, bromine, iodine, amino, nitro, cyano, trifluoromethyl, and phenoxy, and one to three methylene groups may be replaced with carbonyl groups), a straight or branched acyclic unsaturated hydrocarbon having 2 to 14 carbon atoms with 1 to 3 double bonds and/or triple bonds (wherein the acyclic unsaturated hydrocarbon may have at least one substituent selected from the group consisting of alkoxy having 1 to 5 carbon atoms, alkanoyloxy having 1 to 5 carbon atoms, hydroxy, fluorine, chlorine, bromine, iodine, amino, nitro, cyano, trifluoromethyl, or phenoxy, and one to three methylene groups may be replaced with carbonyl groups), or a straight or branched, saturated or unsaturated hydrocarbon having 1 to 14 carbon atoms with one to five thioether, ether and/or amino linkages (wherein the hetero atom does not bond to A directly, and one to three methylene groups may be replaced with carbonyl groups); and $R^5$ is hydrogen or an organic group having any one of the following fundamental structures:

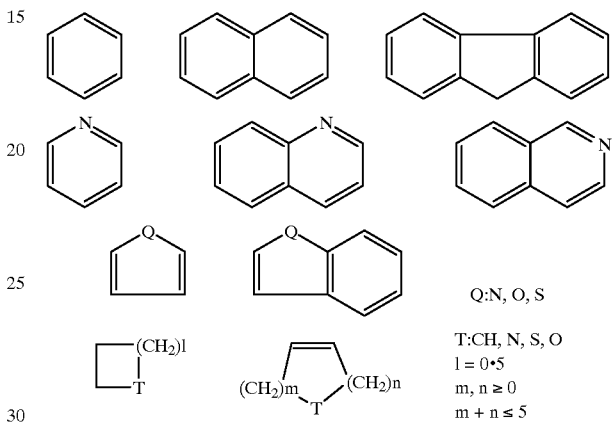

Q:N, O, S
T:CH, N, S, O
l = 0·5
m, n ≥ 0
m + n ≤ 5 wherein the organic group may have at least one substituent selected from the group consisting of alkyl having 1 to 5 carbon atoms, alkoxy having 1 to 5 carbon atoms, alkanoyloxy having 1 to 5 carbon atoms, hydroxy, fluorine, chlorine, bromine, iodine, amino, nitro, cyano, isothiocyanato, trifluoromethyl, trifluoromethoxy, and methylenedioxy; $R^6$ is hydrogen; $R^7$ is hydrogen, hydroxy, alkoxy having 1 to 5 carbon atoms, or alkanoyloxy having 1 to 5 carbon atoms, or $R^6$ and $R^7$ are —O—, —$CH_2$—, —S— together; $R^8$ is hydrogen, alkyl having 1 to 5 carbon atoms or alkanoyl having 1 to 5 carbon atoms; and the general formula (I) comprises (+), (−), and (±) isomers. And an opiate $\kappa$ receptor agonist represented by the general formula (II):

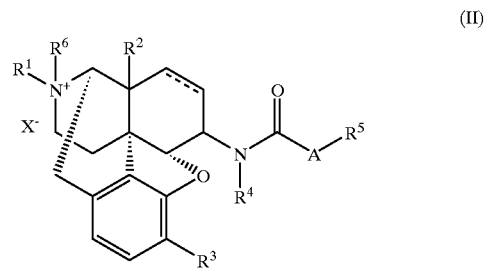

(II)

wherein ═══ is a double bond, or a single bond; $R^1$ is alkyl having 1 to 5 carbon atoms, cycloalkylalkyl having 4 to 7 carbon atoms, cycloalkenylalkyl having 5 to 7 carbon atoms, aralkyl having 7 to 13 carbon atoms, alkenyl having 4 to 7 carbon atoms, or allyl; $R^2$ is hydrogen, hydroxy, nitro, alkanoyloxy having 1 to 5 carbon atoms, alkoxy having 1 to 5 carbon atoms; $R^3$ is hydrogen, hydroxy, alkanoyloxy having 1 to 5 carbon atoms, or alkoxy having 1 to 5 carbon atoms; $R^4$ is hydrogen, a straight or branched alkyl having 1 to 5 carbon atoms, or aryl having 6 to 12 carbon atoms; A is alkylene having 1 to 6 carbon atoms, —CH=CH—, or —C≡C—; and R⁵ is an organic group having any one of the following fundamental structures:

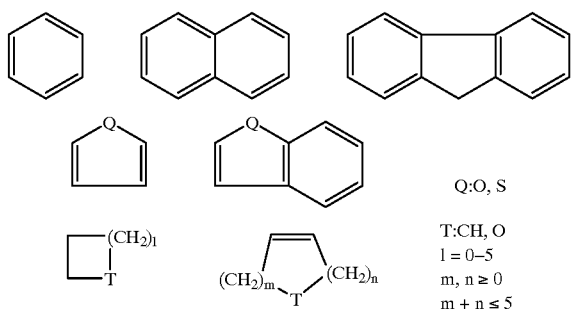

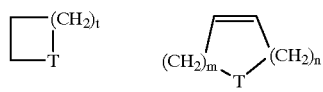

wherein the organic group may have at least one substituent selected from the group consisting of alkyl having 1 to 5 carbon atoms, alkoxy having 1 to 5 carbon atoms, alkanoyloxy having 1 to 5 carbon atoms, hydroxy, fluorine, chlorine, bromine, iodine, nitro, cyano, isothiocyanato, trifluoromethyl, trifluoromethoxy and methylenedioxy; R⁶ is alkyl having 1 to 5 carbon atoms or allyl; X⁻ denotes an anion to form a pharmacologically acceptable salt; and the general formula (II) comprises (+), (−), and (±) isomers. And an opiate κ receptor agonist or its pharmacologically acceptable salt with an added acid represented by the general formula (III):

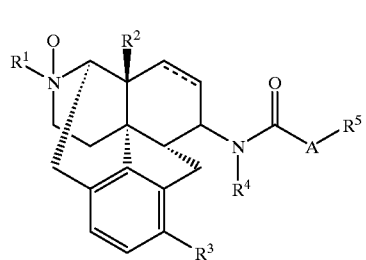

(III)

wherein === is a double bond, or a single bond; R¹ is alkyl having 1 to 5 carbon atoms, cycloalkylalkyl having 4 to 7 carbon atoms, cycloalkenylalkyl having 5 to 7 carbon atoms, aralkyl having 7 to 13 carbon atoms, alkenyl having 4 to 7 carbon atoms, or allyl; R² is hydrogen, hydroxy, nitro, alkanoyloxy having 1 to 5 carbon atoms, alkoxy having 1 to 5 carbon atoms, or alkyl having 1 to 5 carbon atoms; R³ is hydrogen, hydroxy, alkanoyloxy having 1 to 5 carbon atoms, or alkoxy having 1 to 5 carbon atoms; R⁴ is hydrogen, a straight or branched alkyl having 1 to 5 carbon atoms, or aryl having 6 to 12 carbon atoms; A is alkylene having 1 to 6 carbon atoms, —CH=CH—, or —C≡C—; and R⁵ is an organic group having any one of the following fundamental structures:

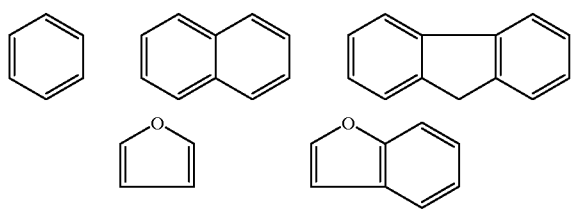

wherein the organic group may have at least one substituent selected from the group consisting of alkyl having 1 to 5 carbon atoms, alkoxy having 1 to 5 carbon atoms, alkanoyloxy having 1 to 5 carbon atoms, hydroxy, fluorine, chlorine, bromine, iodine, nitro, cyano, isothiocyanato, trifluoromethyl, trifluoromethoxy and methylenedioxy; and the general formula (III) comprises (+), (−), and (±) isomers.

A compound to treat pruritus as an opiate κ receptor agonist or its pharmacologically acceptable salt with an added acid other than morphinan derivatives is represented by the general formula (IV):

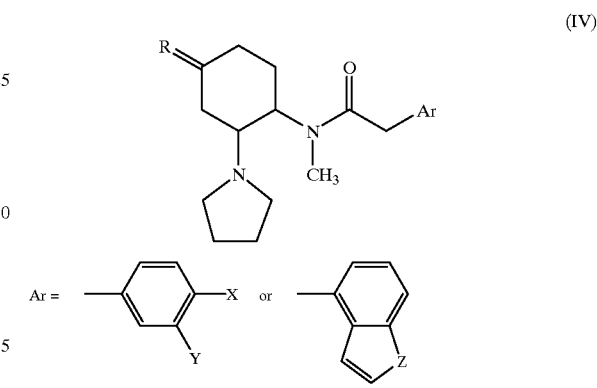

wherein R denotes two hydrogens, or —O—CH₂CH₂CH₂13; X and Y are hydrogen or chlorine; Z is O or S; and the general formula (IV) comprises (+), (−), and (±) isomers. And an opiate κ receptor agonist or its pharmacologically acceptable salt with an added acid represented by the general formula (V):

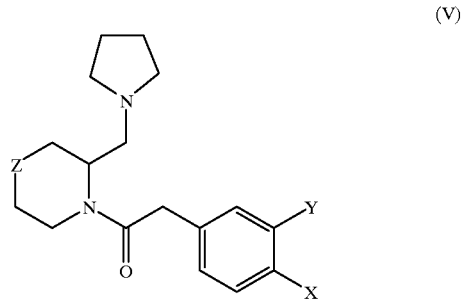

wherein X is hydrogen, chlorine, or trifluoromethyl; Y is hydrogen or chlorine; Z is CH₂, —OCH₂CH₂O—, or NCO₂CH₃; and the general formula (V) comprises (+), (−), and (±) isomer. And an opiate κ receptor agonist or its pharmacologically acceptable salt with an added acid represented by the general formula (VI):

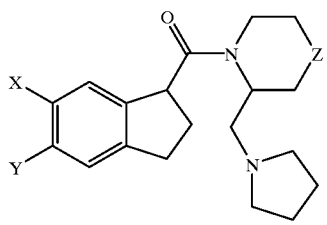

(VI)

wherein X and Y are hydrogen or chlorine; Z is $CH_2$, O, or S; and the general formula (VI) comprises (+), (−), and (±) isomers. And an opiate κ receptor agonist or its pharmacologically accepted salt with an added acid represented by the general formula (VII):

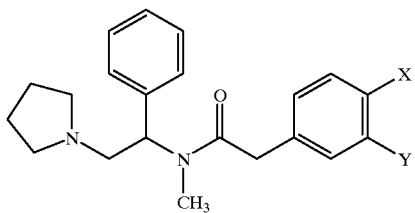

(VII)

wherein X and Y are hydrogen or chlorine; and the general formula (VII) comprises (+), (−), and (±) isomers. One type or several types of opiate κ receptor agonists may be used as effective components.

Examples of dermatoses complicated with pruritus as the subject for treatment include atopic dermatitis, nervous dermatitis, contact dermatitis, seborrheic dermatitis, autosensitization dermatitis, caterpillar dermatitis, asteatosis, senile pruritus cutaneous, insect sting, photosensitive dermatosis, urticaria, prurigo, herpes, impetigo, eczema, tinea, lichen, psoriasis, scabies, and acne vulgarism Typical examples of visceral diseases complicated with pruritus as the subject include malignant tumors, diabetes mellitus, hepatic diseases, renal failure, hemodialysis, and pregnancy. in addition, it can be applied to pruritus being a complication of ophthalmic diseases or otorhinolaryngologic diseases.

Of the compounds belonging to the κ receptor agonists of this invention represented by general formula (I), $R^1$ preferably is alkyl having 1 to 5 carbon atoms, cycloalkylalkyl having 4 to 7 carbon atoms, cycloalkenylalkyl having 5 to 7 carbon atoms, aryl having 6–12 carbon atoms, aralkyl having 7 to 13 carbon atoms, alkenyl having 4 to 7 carbon atoms, allyl, furan-2-yl-alkyl having 1 to 5 carbon atoms, or thiophene-2-yl-alkyl having 1 to 5 carbon atoms; and particularly methyl, ethyl, propyl, butyl, isobutyl, cyclopropylmethyl, allyl, benzyl, phenethyl, furan-2-yl-methyl, or thiophene-2-yl-methyl is preferred.

$R^2$ preferably is hydrogen, hydroxy, nitro, acetoxy, methoxy, methyl, ethyl, propyl, amino, dimethylamino, acetylamino, or benzoylamino; and further hydrogen, hydroxy, nitro, acetoxy, methoxy, methyl or dimethylamino is preferred. Particularly, hydrogen, hydroxy, acetoxy or methoxy is more preferred.

$R^3$ preferably is a hydrogen, hydroxy, acetoxy or methoxy, and particularly hydroxy, acetoxy or methoxy is preferred.

"A" preferably represents, in concrete terms, $-NR^4C(=O)-$, $-NR^4C(=S)-$, $-NR^4C(=O)O-$, $-NR^4C(=O)NR^4-$, $-NR^4C(=S)NR^4-$, $-NR^4C(=O)S-$, $-OC(=O)-$, $-OC(=O)O-$, $-SC(=O)-$, $-NR^4-$, $-O-$, $-NR^4SO_2-$, or $-OSO_2-$; and particularly $-NR^4C(=O)-$, $-NR^4C(=S)-$, $-NR^4C(=O)O-$, $-NR^4C(=O)NR^4-$, $-NR^4C(=S)NR^4-$, or $-NR^4SO_2-$ is preferred. Or preferred is $-XC(=Y)-$ (where X stands for $NR^4$, S, or O, Y for O and $R^4$ for hydogen or alkyl having 1 to 5 carbon atoms), $-XC(=Y)Z-$, $-X-$, or $-XSO_2-$ (where X stands for $NR^4$, Y for O or S, Z for $NR^4$ or O, and $R^4$ for hydrogen or alkyl having 1 to 5 carbon atoms) Further preferred is $-XC(=Y)-$ or $-XC(=Y)Z-$ (where X stands for $NR^4$, Y for O, Z for O, and $R^4$ for alkyl having 1 to 5 carbon atoms). Of them, $-XC(=Y)-$ (where X stands for $NR^4$ Y for O, and $R^4$ for alkyl having 1 to 5 carbon atoms) is more preferred.

$R^4$ is is preferably hydrogen, or straight or branched alkyl having 1 to 5 carbon atoms; and particularly straight or branched alkyl having 1 to 5 carbon atoms is preferred. Of them, methyl, ethyl, propyl, butyl or isobutyl is more preferred.

"B" is preferably $-(CH_2)n-$ (n=0–10), $-(CH_2)n-C(=O)-$(n=1–4), $-CH=CH-(CH_2)n-$ (n=0–4), $-C=C-(CH_2)n-$(n=0–4), $-CH_2-O-$, $-CH_2-S-$, $-(CH_2)_2-O-CH_2-$, or $-CH=CH-CH=CH-(CH_2)n-$(n=0–4). Particularly, $-(CH_2)n-$ (n=1–3), $-CH=CH-(CH_2)n-$(n=0–4), $-C=C-(CH_2)n-$(n=0–4), $-CH_2-O-$ or $-CH_2-S-$ can be cited as preferred examples. Of them, straight-chained alkylene having 1 to 3 carbon atoms, $-CH=CH-$, $-C=C-$, $-CH_2O-$ or $-CH_2S-$ is more preferred. Particularly $-CH=CH-$ or $-C=C-$ is preferred. (of course, these preferred examples include those which have their components substituted by various substitutes as described above, or replaced with such substituents.)

$R^5$ is preferably hyrogen or organic group having any one of the following basic skeletons:

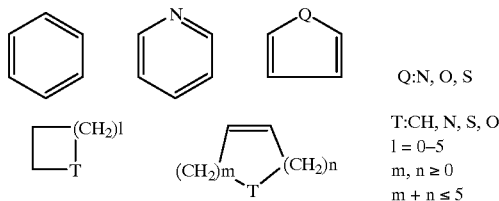

Q:N, O, S

T:CH, N, S, O
l = 0–5
m, n ≥ 0
m + n ≤ 5

(where the organic group may have its component substituted by at least one substituent selected from the group consisting of alkyl having 1 to 5 carbon atoms, alkoxy having 1 to 5 carbon atoms, alkanoyloxy having 1 to 5 carbon atoms, hydroxy, fluorine, chlorine, bromine, iodine, amino, nitro, cyano, isothiocyanato, trifluoromethyl, trifluoromethoxy and methylenedioxy); and, of the compounds cited above with regard to $R^5$, hydrogen, phenyl, thienyl or furanyl (these organic groups may have their component substituted by at least one substituent selected from the group consisting of alkyl having 1 to 5 carbon atoms, alkoxy having 1 to 5 carbon atoms, alkanoyloxy having 1 to 5 carbon atoms, hydroxy, fluorine, chlorine, bromine, iodine, amino, nitro, cyano, isothiocyanato, trifluoromethyl, trifluoromethoxy and methylenedioxy) is more preferred.

More specifically, what is preferred may include hydrogen, phenyl, 2-methylphenyl, 3-methylphenyl, 4-methylphenyl, 3,4-dimethylphenyl, 3,5-dimethylphenyl, 2-methoxyphenyl, 3-methoxyphenyl, 4-methoxyphenyl, 3,4-dimethoxyphenyl, 3-hydroxyphenyl, 4-hydroxyphenyl, 3,4-dihydroxyphenyl, 2-fluorophenyl, 3-fluorophenyl, 4-fluorophenyl, 3,4-difluorophenyl, perfluorophenyl, 2-chlorophenyl, 3-chlorophenyl, 4-chlorophenyl, 2,4-dichlorophenyl, 3,4-dichlorophenyl, 2,4,5-trichlorophenyl, 2,4,6-trichlorophenyl, 2-bromophenyl, 3-bromophenyl, 4-bromophenyl, 2-nitrophenyl, 3-nitrophenyl, 4-nitrophenyl, 2-aminophenyl, 3-aminophenyl, 4-aminophenyl, 2-trifluoromethylphenyl, 3-trifluoromethylphenyl, 4-trifluoromethylphenyl, 2-trifluoromethoxyphenyl, 3-trifluoromethoxyphenyl, 4-trifluoromethoxyphenyl, 3,4-methylenedioxyphenyl, 2-furanyl, 3-furanyl, 2-thienyl, 3-thienyl, cyclopentyl and cyclohexyl, but it should not be limited to above.

$R^6$ and $R^7$ are preferably —O—, —CH$_2$— or —S— together, particularly their being —O— together is preferred.

$R^8$ is preferably hydrogen, alkyl having 1 to 5 carbon atoms, or alkanoyl having 1 to 5 carbons; and, of the compounds cited above, hydrogen, methyl, ethyl or propyl can be cited as preferred examples. Particularly, hydrogen is preferred.

These κ receptor agonists represented by general formula (I) can be prepared by the method disclosed in Japanese Patent No. 2525552.

Further, the compounds represented by general formula (II) are new morphinan derivatives from quaternary ammonium salts, and opiate κ receptor agonists. In that formula, $R^1$ is preferably alkyl having 1 to 5 carbon atoms, cycloalkylalkyl having 4 to 7 carbon atoms, cycloalkenylalkyl having 5 to 7 carbons, aralkyl having 7 to 13 carbon atoms, alkenyl having 4 to 7 carbon atoms, or allyl; and particularly methyl, ethyl, propyl, butyl, isobutyl, cyclopropylmethyl, cyclobutylmethyl, cyclopentylmethyl, cyclopentenylmethyl, cyclohexynylmethyl, benzyl, phenethyl, trans-2-butenyl, 2-methyl-2-butenyl, or allyl is preferred. More preferred is methyl, ethyl, propyl, butyl, isobutyl, cyclopropylmethyl, benzyl, phenethyl or allyl.

$R^2$ is preferably hydrogen, hydroxy, nitro, acetoxy, methoxy, methyl, ethyl or propyl; and particularly hydrogen, hydroxy, acetoxy or methoxy is preferred.

$R^3$ is preferably hydrogen, hydroxy, alkanoyloxy having 1 to 5 carbons, or alkoxy having 1 to 5 carbon atoms; and particularly hydroxy, acetoxy or methoxy is preferred.

$R^4$ is preferably hydrogen, straight or branched alkyl having 1 to 5 carbon atoms, or aryl having 6 to 12 carbon atoms; and particularly straight or branched alkyl having 1 to 5 carbon atoms, or, of them, methyl, ethyl, propyl, isopropyl, butyl or isobutyl is preferred.

"A" is preferably alkylene having 1 to 6 carbon atoms, —CH=CH—, or —C≡C—; and, of them, —CH=CH— or —C≡C— is more preferred.

$R^5$ is preferably an organic group having any one of the following basic skeletons:

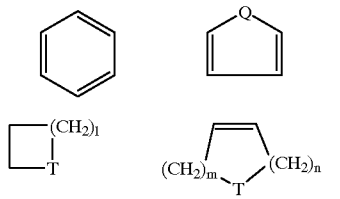

Q:O, S

T:CH, O
l = 0–5
m, n ≥ 0
m + n ≤ 5 where the organic group may have its component substituted by at least one substituent selected from the group consisting of alkyl having 1 to 5 carbon atoms, alkoxy having 1 to 5 carbon atoms, alkanoyloxy having 1 to 5 carbon atoms, hydroxy, fluorine, chlorine, bromine, iodine, nitro, cyano, isothiocyanato, trifluoromethyl, trifluoromethoxy and methylenedioxy and particularly phenyl, 2-chlorophenyl, 3-chlorophenyl, 4-chlorophenyl, 3,4-dichlorophenyl, 2-fluorophenyl, 3-fluorophenyl, 4-fluorophenyl, 3,4-difluorophenyl, 2-bromophenyl, 3-bromophenyl, 4-bromophenyl, 2-nitrophenyl, 3-nitrophenyl, 4-nitrophenyl, 2-trifluoromethylphenyl, 3-trifluoromethylphenyl, 4-trifluoromethylphenyl, 2-trifluoromethoxyphenyl, 3-trifluoromethoxyphenyl, 4-trifluoromethoxyphenyl, 2-methylphenyl, 3-methylphenyl, 4-methylphenyl, 3,4-dimethylphenyl, 2-methoxyphenyl, 3-methoxyphenyl, 4-methoxyphenyl, 3,4-dimethoxyphenyl, 2-hydroxyphenyl, 3-hydroxyphenyl, 4-hydroxyphenyl, 3,4-dihydroxyphenyl, 3-furanyl, 2-furanyl, 3-thienyl, 2-thienyl, cyclopentyl, or cyclohexyl is preferred, but what is preferred should not be limited to them.

$R^6$ is preferably alkyl having 1 to 5 carbon atoms or allyl; particularly methyl is preferred.

The pharmacologically acceptable, ion-supplementing salt $X^-$ may preferably include iodide ions, bromide ions, chloride ions, methanesulfonate and the like, but of course it should not be limited to them.

Concrete examples of the compounds as represented by general formula (II) are shown in Table 1. The compounds represented by general formula (II) comprise (+), (−) and (±) isomers.

TABLE 1

| Q | R1 | R2 | R3 |
|---|----|----|----|
| O | H | H | H |
| O | CH3 | H | H |
| O | H | CH3 | H |
| O | H | H | CH3 |
| O | F | H | H |
| O | H | F | H |
| O | H | H | F |
| O | Cl | H | H |
| O | H | Cl | H |
| O | H | H | Cl |
| O | Br | H | H |
| O | H | Br | H |
| O | H | H | Br |
| O | CF3 | H | H |
| O | H | CF3 | H |
| O | H | H | CF3 |
| O | CN | H | H |
| O | H | CN | H |
| O | H | H | CN |
| S | H | H | H |
| S | CH3 | H | H |
| S | H | CH3 | H |
| S | H | H | CH3 |
| S | F | H | H |
| S | H | F | H |
| S | H | H | F |
| S | Cl | H | H |
| S | H | Cl | H |
| S | H | H | Cl |

TABLE 1-continued

| | | | |
|---|---|---|---|
| S | Br | H | H |
| S | H | Br | H |
| S | H | H | Br |
| S | CF3 | H | H |
| S | H | CF3 | H |
| S | H | H | CF3 |
| S | CN | H | H |
| S | H | CN | H |
| S | H | H | CN |

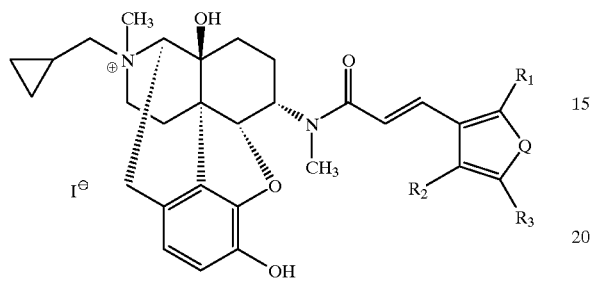

| | | | |
|---|---|---|---|
| O | H | H | H |
| O | CH3 | H | H |
| O | H | CH3 | H |
| O | H | H | CH3 |
| O | F | H | H |
| O | H | F | H |
| O | H | H | F |
| O | Cl | H | H |
| O | H | Cl | H |
| O | H | H | Cl |
| O | Br | H | H |
| O | H | Br | H |
| O | H | H | Br |
| O | CF3 | H | H |
| O | H | CF3 | H |
| O | H | H | CF3 |
| O | CN | H | H |
| O | H | CN | H |
| O | H | H | CN |
| S | H | H | H |
| S | CH3 | H | H |
| S | H | CH3 | H |
| S | H | H | CH3 |
| S | F | H | H |
| S | H | F | H |
| S | H | H | F |
| S | Cl | H | H |
| S | H | Cl | H |
| S | H | H | Cl |
| S | Br | H | H |
| S | H | Br | H |
| S | H | H | Br |
| S | CF3 | H | H |
| S | H | CF3 | H |
| S | H | H | CF3 |
| S | CN | H | H |
| S | H | CN | H |
| S | H | H | CN |

TABLE 1-continued

| | | | |
|---|---|---|---|
| O | CH3 | H | H |
| O | H | CH3 | H |
| O | H | H | CH3 |
| O | F | H | H |
| O | H | F | H |
| O | H | H | F |
| O | Cl | H | H |
| O | H | Cl | H |
| O | H | H | Cl |
| O | Br | H | H |
| O | H | Br | H |
| O | H | H | Br |
| O | CF3 | H | H |
| O | H | CF3 | H |
| O | H | H | CF3 |
| O | CN | H | H |
| O | H | CN | H |
| O | H | H | CN |
| S | H | H | H |
| S | CH3 | H | H |
| S | H | CH3 | H |
| S | H | H | CH3 |
| S | F | H | H |
| S | H | F | H |
| S | H | H | F |
| S | Cl | H | H |
| S | H | Cl | H |
| S | H | H | Cl |
| S | Br | H | H |
| S | H | Br | H |
| S | H | H | Br |
| S | CF3 | H | H |
| S | H | CF3 | H |
| S | H | H | CF3 |
| S | CN | H | H |
| S | H | CN | H |
| S | H | H | CN |

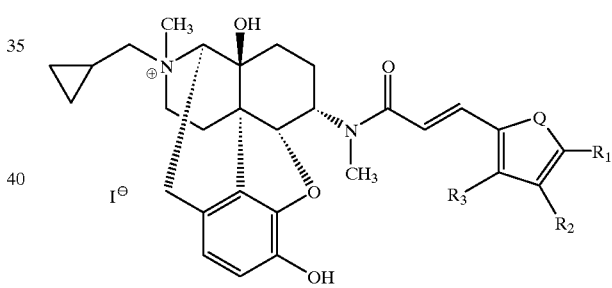

| | | | |
|---|---|---|---|
| O | H | H | H |
| O | CH3 | H | H |
| O | H | CH3 | H |
| O | H | H | CH3 |
| O | F | H | H |
| O | H | F | H |
| O | H | H | F |
| O | Cl | H | H |
| O | H | Cl | H |
| O | H | H | Cl |
| O | Br | H | H |
| O | H | Br | H |
| O | H | H | Br |
| O | CF3 | H | H |
| O | H | CF3 | H |
| O | H | H | CF3 |
| O | CN | H | H |
| O | H | CN | H |
| O | H | H | CN |
| S | H | H | H |
| S | CH3 | H | H |
| S | H | CH3 | H |
| S | H | H | CH3 |
| S | F | H | H |
| S | H | F | H |
| S | H | H | F |

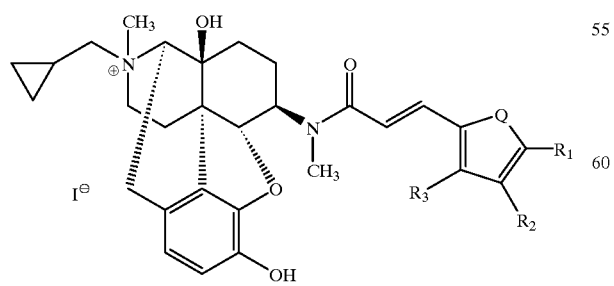

| | | | |
|---|---|---|---|
| O | H | H | H |

TABLE 1-continued

| | | | |
|---|---|---|---|
| S | Cl | H | H |
| S | H | Cl | H |
| S | H | H | Cl |
| S | Br | H | H |
| S | H | Br | H |
| S | H | H | Br |
| S | CF3 | H | H |
| S | H | CF3 | H |
| S | H | H | CF3 |
| S | CN | H | H |
| S | H | CN | H |
| S | H | H | CN |

| R1 | R2 | R3 | R4 |
|---|---|---|---|

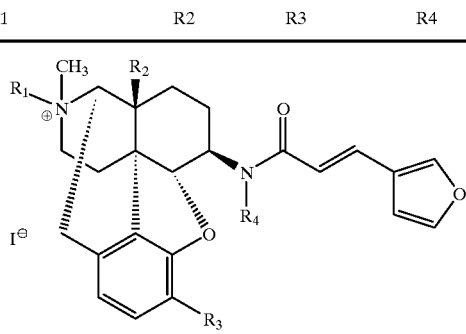

| R1 | R2 | R3 | R4 |
|---|---|---|---|
| C3H5CH2 | OH | OAc | CH3 |
| C3H5CH2 | OH | OCH3 | CH3 |
| C3H5CH2 | OH | H | CH3 |
| C3H5CH2 | OAc | OH | CH3 |
| C3H5CH2 | OAc | OAc | CH3 |
| C3H5CH2 | OAc | OCH3 | CH3 |
| C3H5CH2 | OAc | H | CH3 |
| C3H5CH2 | OCH3 | OH | CH3 |
| C3H5CH2 | OCH3 | OAc | CH3 |
| C3H5CH2 | OCH3 | OCH3 | CH3 |
| C3H5CH2 | OCH3 | H | CH3 |
| C3H5CH2 | OH | OH | C2H5 |
| C3H5CH2 | OH | OH | n-C3H7 |
| C3H5CH2 | OH | OH | i-C3H7 |
| C3H5CH2 | OH | OH | n-C4H9 |
| C3H5CH2 | OH | OH | i-C4H9 |
| CH3 | OH | OH | CH3 |
| CH3 | OH | OAc | CH3 |
| CH3 | OH | OCH3 | CH3 |
| CH3 | OAc | OH | CH3 |
| CH3 | OAc | OAc | CH3 |
| CH3 | OAc | OCH3 | CH3 |
| CH3 | OCH3 | OH | CH3 |
| CH3 | OCH3 | OAc | CH3 |
| CH3 | OCH3 | OCH3 | CH3 |
| CH3 | OH | OH | C2H5 |
| CH3 | OH | OH | n-C3H7 |
| CH3 | OH | OH | i-C3H7 |
| CH3 | OH | OH | n-C4H9 |
| CH3 | OH | OH | i-C4H9 |
| CH2CHCH2 | OH | OH | CH3 |
| CH2CHCH2 | OH | OAc | CH3 |
| CH2CHCH2 | OH | OCH3 | CH3 |
| CH2CHCH2 | OAc | OH | CH3 |
| CH2CHCH2 | OAc | OAc | CH3 |
| CH2CHCH2 | OAc | OCH3 | CH3 |
| CH2CHCH2 | OCH3 | OH | CH3 |
| CH2CHCH2 | OCH3 | OAc | CH3 |
| CH2CHCH2 | OCH3 | OCH3 | CH3 |
| CH2CHCH2 | OH | OH | C2H5 |
| CH2CHCH2 | OH | OH | n-C3H7 |
| CH2CHCH2 | OH | OH | i-C3H7 |
| CH2CHCH2 | OH | OH | n-C4H9 |
| CH2CHCH2 | OH | OH | i-C4H9 |
| CH2CHCH2 | OH | OAc | C2H5 |
| PhCH2CH2 | OH | OH | CH3 |
| PhCH2CH2 | OH | OAc | CH3 |
| PhCH2CH2 | OH | OCH3 | CH3 |
| PhCH2CH2 | OAc | OH | CH3 |
| PhCH2CH2 | OAc | OAc | CH3 |
| PhCH2CH2 | OAc | OCH3 | CH3 |
| PhCH2CH2 | OCH3 | OH | CH3 |
| PhCH2CH2 | OCH3 | OAc | CH3 |
| PhCH2CH2 | OCH3 | OCH3 | CH3 |
| PhCH2CH2 | OH | OH | C2H5 |
| PhCH2CH2 | OH | OH | n-C3H7 |
| PhCH2CH2 | OH | OH | i-C3H7 |
| PhCH2CH2 | OH | OH | n-C4H9 |
| PhCH2CH2 | OH | OH | i-C4H9 |
| PhCH2CH2 | OH | OAc | C2H5 |

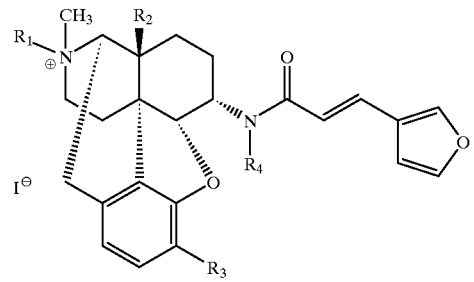

| R1 | R2 | R3 | R4 |
|---|---|---|---|
| C3H5CH2 | OH | OAc | CH3 |
| C3H5CH2 | OH | OCH3 | CH3 |
| C3H5CH2 | OH | H | CH3 |
| C3H5CH2 | OAc | OH | CH3 |
| C3H5CH2 | OAc | OAc | CH3 |
| C3H5CH2 | OAc | OCH3 | CH3 |
| C3H5CH2 | OAc | H | CH3 |
| C3H5CH2 | OCH3 | OH | CH3 |
| C3H5CH2 | OCH3 | OAc | CH3 |
| C3H5CH2 | OCH3 | OCH3 | CH3 |
| C3H5CH2 | OCH3 | H | CH3 |
| C3H5CH2 | OH | OH | C2H5 |
| C3H5CH2 | OH | OH | n-C3H7 |
| C3H5CH2 | OH | OH | i-C3H7 |
| C3H5CH2 | OH | OH | n-C4H9 |
| C3H5CH2 | OH | OH | i-C4H9 |
| CH3 | OH | OH | CH3 |
| CH3 | OH | OAc | CH3 |
| CH3 | OH | OCH3 | CH3 |
| CH3 | OAc | OH | CH3 |
| CH3 | OAc | OAc | CH3 |
| CH3 | OAc | OCH3 | CH3 |
| CH3 | OCH3 | OH | CH3 |
| CH3 | OCH3 | OAc | CH3 |
| CH3 | OCH3 | OCH3 | CH3 |
| CH3 | OH | OH | C2H5 |
| CH3 | OH | OH | n-C3H7 |
| CH3 | OH | OH | i-C3H7 |
| CH3 | OH | OH | n-C4H9 |
| CH3 | OH | OH | i-C4H9 |
| CH2CHCH2 | OH | OH | CH3 |
| CH2CHCH2 | OH | OAc | CH3 |
| CH2CHCH2 | OH | OCH3 | CH3 |
| CH2CHCH2 | OAc | OH | CH3 |
| CH2CHCH2 | OAc | OAc | CH3 |
| CH2CHCH2 | OAc | OCH3 | CH3 |
| CH2CHCH2 | OCH3 | OH | CH3 |
| CH2CHCH2 | OCH3 | OAc | CH3 |
| CH2CHCH2 | OCH3 | OCH3 | CH3 |
| CH2CHCH2 | OH | OH | C2H5 |
| CH2CHCH2 | OH | OH | n-C3H7 |
| CH2CHCH2 | OH | OH | i-C3H7 |
| CH2CHCH2 | OH | OH | n-C4H9 |
| CH2CHCH2 | OH | OH | i-C4H9 |
| CH2CHCH2 | OH | OAc | C2H5 |
| PhCH2CH2 | OH | OH | CH3 |
| PhCH2CH2 | OH | OAc | CH3 |
| PhCH2CH2 | OH | OCH3 | CH3 |
| PhCH2CH2 | OAc | OH | CH3 |
| PhCH2CH2 | OAc | OAc | CH3 |
| PhCH2CH2 | OAc | OCH3 | CH3 |
| PhCH2CH2 | OCH3 | OH | CH3 |

TABLE 1-continued

| PhCH2CH2 | OCH3 | OAc | CH3 |
| --- | --- | --- | --- |
| PhCH2CH2 | OCH3 | OCH3 | CH3 |
| PhCH2CH2 | OH | OH | C2H5 |
| PhCH2CH2 | OH | OH | n-C3H7 |
| PhCH2CH2 | OH | OH | i-C3H7 |
| PhCH2CH2 | OH | OH | n-C4H9 |
| PhCH2CH2 | OH | OH | i-C4H9 |
| PhCH2CH2 | OH | OAc | C2H5 |

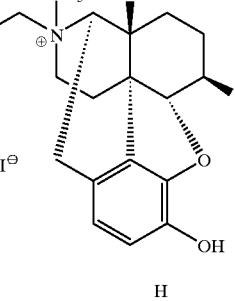

| H | H | H | CH3 |
| --- | --- | --- | --- |
| H | H | H | C2H5 |
| CH3 | H | H | CH3 |
| H | CH3 | H | CH3 |
| H | H | CH3 | CH3 |
| H | CH3 | CH3 | CH3 |
| H | CH3 | H | C2H5 |
| H | CH3 | H | n-C3H7 |
| H | CH3 | H | i-C3H7 |
| H | CH3 | H | n-C4H9 |
| H | CH3 | H | i-C4H9 |
| OCH3 | H | H | CH3 |
| H | OCH3 | H | CH3 |
| H | H | OCH3 | CH3 |
| H | OCH3 | OCH3 | CH3 |
| H | OCH3 | H | C2H5 |
| H | OCH3 | H | n-C3H7 |
| H | OCH3 | H | i-C3H7 |
| H | OCH3 | H | n-C4H9 |
| H | OCH3 | H | i-C4H9 |
| OH | H | H | CH3 |
| H | OH | H | CH3 |
| H | H | OH | CH3 |
| Cl | H | H | CH3 |
| H | Cl | H | CH3 |
| H | H | Cl | CH3 |
| H | Cl | Cl | CH3 |
| H | Cl | Cl | n-C3H7 |
| H | Cl | Cl | n-C4H9 |
| Br | H | H | CH3 |
| H | Br | H | CH3 |
| H | H | Br | CH3 |
| H | Br | Br | CH3 |
| H | Br | Br | C2H5 |
| F | H | H | CH3 |
| H | F | H | CH3 |
| H | H | F | CH3 |
| H | F | F | CH3 |
| H | F | F | C2H5 |
| NO2 | H | H | CH3 |
| H | NO2 | H | CH3 |
| H | H | NO2 | CH3 |
| CF3 | H | H | CH3 |
| H | CF3 | H | CH3 |
| H | H | CF3 | CH3 |
| H | H | CF3 | C2H5 |
| H | H | CF3 | n-C3H7 |
| H | H | CF3 | i-C3H7 |
| H | H | CF3 | n-C4H9 |
| H | H | CF3 | i-C4H9 |
| OCF3 | H | H | CH3 |
| H | OCF3 | H | CH3 |
| H | H | OCF3 | CH3 |
| H | OCF3 | H | C2H5 |
| H | OCF3 | H | n-C3H7 |
| H | OCF3 | H | i-C3H7 |
| H | OCF3 | CF3 | n-C4H9 |
| H | OCF3 | H | i-C4H9 |

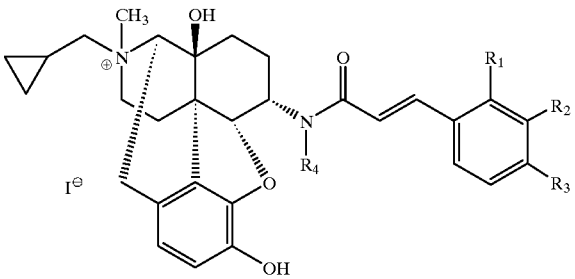

| H | H | H | CH3 |
| --- | --- | --- | --- |
| H | H | H | C2H5 |
| CH3 | H | H | CH3 |
| H | CH3 | H | CH3 |
| H | H | CH3 | CH3 |
| H | CH3 | CH3 | CH3 |
| H | CH3 | H | C2H5 |
| H | CH3 | H | n-C3H7 |
| H | CH3 | H | i-C3H7 |
| H | CH3 | H | n-C4H9 |
| H | CH3 | H | i-C4H9 |
| OCH3 | H | H | CH3 |
| H | OCH3 | H | CH3 |
| H | H | OCH3 | CH3 |
| H | OCH3 | OCH3 | CH3 |
| H | OCH3 | H | C2H5 |
| H | OCH3 | H | n-C3H7 |
| H | OCH3 | H | i-C3H7 |
| H | OCH3 | H | n-C4H9 |
| H | OCH3 | H | i-C4H9 |
| OH | H | H | CH3 |
| H | OH | H | CH3 |
| H | H | OH | CH3 |
| Cl | H | H | CH3 |
| H | Cl | H | CH3 |
| H | H | Cl | CH3 |
| H | Cl | Cl | CH3 |
| H | Cl | Cl | n-C3H7 |
| H | Cl | Cl | n-C4H9 |
| Br | H | H | CH3 |
| H | Br | H | CH3 |
| H | H | Br | CH3 |
| H | Br | Br | CH3 |
| H | Br | Br | C2H5 |
| F | H | H | CH3 |
| H | F | H | CH3 |
| H | H | F | CH3 |
| H | F | F | CH3 |
| H | F | F | C2H5 |
| NO2 | H | H | CH3 |
| H | NO2 | H | CH3 |
| H | H | NO2 | CH3 |
| CF3 | H | H | CH3 |
| H | CF3 | H | CH3 |
| H | H | CF3 | CH3 |
| H | H | CF3 | C2H5 |
| H | H | CF3 | n-C3H7 |
| H | H | CF3 | i-C3H7 |
| H | H | CF3 | n-C4H9 |
| H | H | CF3 | i-C4H9 |
| OCF3 | H | H | CH3 |
| H | OCF3 | H | CH3 |
| H | H | OCF3 | CH3 |
| H | OCF3 | H | C2H5 |
| H | OCF3 | H | n-C3H7 |
| H | OCF3 | H | i-C3H7 |
| H | OCF3 | CF3 | n-C4H9 |
| H | OCF3 | H | i-C4H9 |

TABLE 1-continued

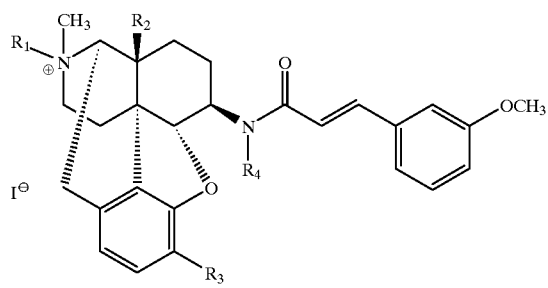

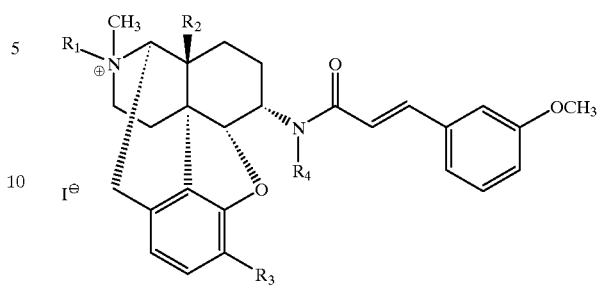

| R1 | R2 | R3 | R4 |
|---|---|---|---|
| C3H5CH2 | OH | OAc | CH3 |
| C3H5CH2 | OH | OCH3 | CH3 |
| C3H5CH2 | OH | H | CH3 |
| C3H5CH2 | OAc | OH | CH3 |
| C3H5CH2 | OAc | OAc | CH3 |
| C3H5CH2 | OAc | OCH3 | CH3 |
| C3H5CH2 | OAc | H | CH3 |
| C3H5CH2 | OCH3 | OH | CH3 |
| C3H5CH2 | OCH3 | OAc | CH3 |
| C3H5CH2 | OCH3 | OCH3 | CH3 |
| C3H5CH2 | OCH3 | H | CH3 |
| CH3 | OH | OH | CH3 |
| CH3 | OH | OAc | CH3 |
| CH3 | OH | OCH3 | CH3 |
| CH3 | OAc | OH | CH3 |
| CH3 | OAc | OAc | CH3 |
| CH3 | OAc | OCH3 | CH3 |
| CH3 | OCH3 | OH | CH3 |
| CH3 | OCH3 | OAc | CH3 |
| CH3 | OCH3 | OCH3 | CH3 |
| CH3 | OH | OH | C2H5 |
| CH3 | OH | OH | n-C3H7 |
| CH3 | OH | OH | i-C3H7 |
| CH3 | OH | OH | n-C4H9 |
| CH3 | OH | OH | i-C4H9 |
| CH2CHCH2 | OH | OH | CH3 |
| CH2CHCH2 | OH | OAc | CH3 |
| CH2CHCH2 | OH | OCH3 | CH3 |
| CH2CHCH2 | OAc | OH | CH3 |
| CH2CHCH2 | OAc | OAc | CH3 |
| CH2CHCH2 | OAc | OCH3 | CH3 |
| CH2CHCH2 | OCH3 | OH | CH3 |
| CH2CHCH2 | OCH3 | OAc | CH3 |
| CH2CHCH2 | OCH3 | OCH3 | CH3 |
| CH2CHCH2 | OH | OH | C2H5 |
| CH2CHCH2 | OH | OH | n-C3H7 |
| CH2CHCH2 | OH | OH | i-C3H7 |
| CH2CHCH2 | OH | OH | n-C4H9 |
| CH2CHCH2 | OH | OH | i-C4H9 |
| PhCH2CH2 | OH | OH | CH3 |
| PhCH2CH2 | OH | OAc | CH3 |
| PhCH2CH2 | OH | OCH3 | CH3 |
| PhCH2CH2 | OAc | OH | CH3 |
| PhCH2CH2 | OAc | OAc | CH3 |
| PhCH2CH2 | OAc | OCH3 | CH3 |
| PhCH2CH2 | OCH3 | OH | CH3 |
| PhCH2CH2 | OCH3 | OAc | CH3 |
| PhCH2CH2 | OCH3 | OCH3 | CH3 |
| PhCH2CH2 | OH | OH | C2H5 |
| PhCH2CH2 | OH | OH | n-C3H7 |
| PhCH2CH2 | OH | OH | i-C3H7 |
| PhCH2CH2 | OH | OH | n-C4H9 |
| PhCH2CH2 | OH | OH | i-C4H9 |

TABLE 1-continued

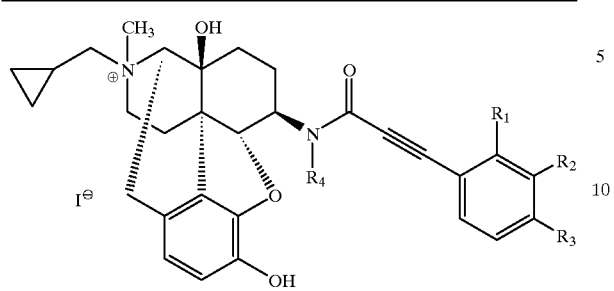

| | | | |
|---|---|---|---|
| H | H | H | CH3 |
| H | H | H | C2H5 |
| CH3 | H | H | CH3 |
| H | CH3 | H | CH3 |
| H | H | CH3 | CH3 |
| H | CH3 | CH3 | CH3 |
| H | CH3 | H | C2H5 |
| H | CH3 | H | n-C3H7 |
| H | CH3 | H | i-C3H7 |
| H | CH3 | H | n-C4H9 |
| H | CH3 | H | i-C4H9 |
| OCH3 | H | H | CH3 |
| H | OCH3 | H | CH3 |
| H | H | OCH3 | CH3 |
| H | OCH3 | OCH3 | CH3 |
| H | OCH3 | H | C2H5 |
| H | OCH3 | H | n-C3H7 |
| H | OCH3 | H | i-C3H7 |
| H | OCH3 | H | n-C4H9 |
| H | OCH3 | H | i-C4H9 |
| OH | H | H | CH3 |
| H | OH | H | CH3 |
| H | H | OH | CH3 |
| Cl | H | H | CH3 |
| H | Cl | H | CH3 |
| H | H | Cl | CH3 |
| H | Cl | Cl | CH3 |
| H | Cl | Cl | n-C3H7 |
| H | Cl | Cl | n-C4H9 |
| Br | H | H | CH3 |
| H | Br | H | CH3 |
| H | H | Br | CH3 |
| H | Br | Br | CH3 |
| H | Br | Br | C2H5 |
| F | H | H | CH3 |
| H | F | H | CH3 |
| H | H | F | CH3 |
| H | F | F | CH3 |
| H | F | F | C2H5 |
| NO2 | H | H | CH3 |
| H | NO2 | H | CH3 |
| H | H | NO2 | CH3 |
| CF3 | H | H | CH3 |
| H | CF3 | H | CH3 |
| H | H | CF3 | CH3 |
| H | H | CF3 | C2H5 |
| H | H | CF3 | n-C3H7 |
| H | H | CF3 | i-C3H7 |
| H | H | CF3 | n-C4H9 |
| H | H | CF3 | i-C4H9 |
| OCF3 | H | H | CH3 |
| H | OCF3 | H | CH3 |
| H | H | OCF3 | CH3 |
| H | OCF3 | H | C2H5 |
| H | OCF3 | H | n-C3H7 |
| H | OCF3 | H | i-C3H7 |
| H | OCF3 | CF3 | n-C4H9 |
| H | OCF3 | H | i-C4H9 |

TABLE 1-continued

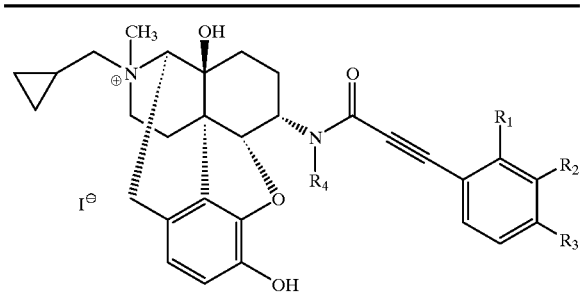

| | | | |
|---|---|---|---|
| H | H | H | CH3 |
| H | H | H | C2H5 |
| CH3 | H | H | CH3 |
| H | CH3 | H | CH3 |
| H | H | CH3 | CH3 |
| H | CH3 | CH3 | CH3 |
| H | CH3 | H | C2H5 |
| H | CH3 | H | n-C3H7 |
| H | CH3 | H | i-C3H7 |
| H | CH3 | H | n-C4H9 |
| H | CH3 | H | i-C4H9 |
| OCH3 | H | H | CH3 |
| H | OCH3 | H | CH3 |
| H | H | OCH3 | CH3 |
| H | OCH3 | OCH3 | CH3 |
| H | OCH3 | H | C2H5 |
| H | OCH3 | H | n-C3H7 |
| H | OCH3 | H | i-C3H7 |
| H | OCH3 | H | n-C4H9 |
| H | OCH3 | H | i-C4H9 |
| OH | H | H | CH3 |
| H | OH | H | CH3 |
| H | H | OH | CH3 |
| Cl | H | H | CH3 |
| H | Cl | H | CH3 |
| H | H | Cl | CH3 |
| H | Cl | Cl | CH3 |
| H | Cl | Cl | n-C3H7 |
| H | Cl | Cl | n-C4H9 |
| Br | H | H | CH3 |
| H | Br | H | CH3 |
| H | H | Br | CH3 |
| H | Br | Br | CH3 |
| H | Br | Br | C2H5 |
| F | H | H | CH3 |
| H | F | H | CH3 |
| H | H | F | CH3 |
| H | F | F | CH3 |
| H | F | F | C2H5 |
| NO2 | H | H | CH3 |
| H | NO2 | H | CH3 |
| H | H | NO2 | CH3 |
| CF3 | H | H | CH3 |
| H | CF3 | H | CH3 |
| H | H | CF3 | CH3 |
| H | H | CF3 | C2H5 |
| H | H | CF3 | n-C3H7 |
| H | H | CF3 | i-C3H7 |
| H | H | CF3 | n-C4H9 |
| H | H | CF3 | i-C4H9 |
| OCF3 | H | H | CH3 |
| H | OCF3 | H | CH3 |
| H | H | OCF3 | CH3 |
| H | OCF3 | H | C2H5 |
| H | OCF3 | H | n-C3H7 |
| H | OCF3 | H | i-C3H7 |
| H | OCF3 | CF3 | n-C4H9 |
| H | OCF3 | H | i-C4H9 |

TABLE 1-continued

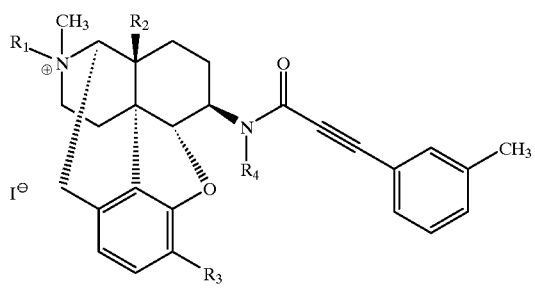

| | | | |
|---|---|---|---|
| C3H5CH2 | OH | OAc | CH3 |
| C3H5CH2 | OH | OCH3 | CH3 |
| C3H5CH2 | OH | H | CH3 |
| C3H5CH2 | OAc | OH | CH3 |
| C3H5CH2 | OAc | OAc | CH3 |
| C3H5CH2 | OAc | OCH3 | CH3 |
| C3H5CH2 | OAc | H | CH3 |
| C3H5CH2 | OCH3 | OH | CH3 |
| C3H5CH2 | OCH3 | OAc | CH3 |
| C3H5CH2 | OCH3 | OCH3 | CH3 |
| C3H5CH2 | OCH3 | H | CH3 |
| CH3 | OH | OH | CH3 |
| CH3 | OH | OAc | CH3 |
| CH3 | OH | OCH3 | CH3 |
| CH3 | OAc | OH | CH3 |
| CH3 | OAc | OAc | CH3 |
| CH3 | OAc | OCH3 | CH3 |
| CH3 | OCH3 | OH | CH3 |
| CH3 | OCH3 | OAc | CH3 |
| CH3 | OCH3 | OCH3 | CH3 |
| CH3 | OH | OH | C2H5 |
| CH3 | OH | OH | n-C3H7 |
| CH3 | OH | OH | i-C3H7 |
| CH3 | OH | OH | n-C4H9 |
| CH3 | OH | OH | i-C4H9 |
| CH2CHCH2 | OH | OH | CH3 |
| CH2CHCH2 | OH | OAc | CH3 |
| CH2CHCH2 | OH | OCH3 | CH3 |
| CH2CHCH2 | OAc | OH | CH3 |
| CH2CHCH2 | OAc | OAc | CH3 |
| CH2CHCH2 | OAc | OCH3 | CH3 |
| CH2CHCH2 | OCH3 | OH | CH3 |
| CH2CHCH2 | OCH3 | OAc | CH3 |
| CH2CHCH2 | OCH3 | OCH3 | CH3 |
| CH2CHCH2 | OH | OH | C2H5 |
| CH2CHCH2 | OH | OH | n-C3H7 |
| CH2CHCH2 | OH | OH | i-C3H7 |
| CH2CHCH2 | OH | OH | n-C4H9 |
| CH2CHCH2 | OH | OH | i-C4H9 |
| PhCH2CH2 | OH | OH | CH3 |
| PhCH2CH2 | OH | OAc | CH3 |
| PhCH2CH2 | OH | OCH3 | CH3 |
| PhCH2CH2 | OAc | OH | CH3 |
| PhCH2CH2 | OAc | OAc | CH3 |
| PhCH2CH2 | OAc | OCH3 | CH3 |
| PhCH2CH2 | OCH3 | OH | CH3 |
| PhCH2CH2 | OCH3 | OAc | CH3 |
| PhCH2CH2 | OCH3 | OCH3 | CH3 |
| PhCH2CH2 | OH | OH | C2H5 |
| PhCH2CH2 | OH | OH | n-C3H7 |
| PhCH2CH2 | OH | OH | i-C3H7 |
| PhCH2CH2 | OH | OH | n-C4H9 |
| PhCH2CH2 | OH | OH | i-C4H9 |

TABLE 1-continued

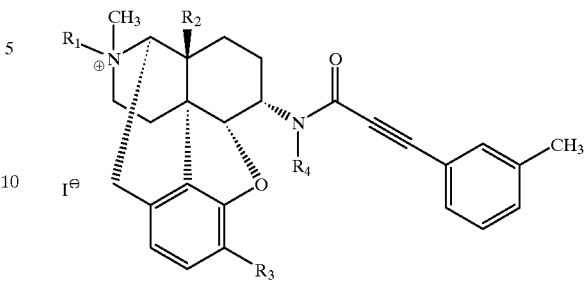

| | | | |
|---|---|---|---|
| C3H5CH2 | OH | OAc | CH3 |
| C3H5CH2 | OH | OCH3 | CH3 |
| C3H5CH2 | OH | H | CH3 |
| C3H5CH2 | OAc | OH | CH3 |
| C3H5CH2 | OAc | OAc | CH3 |
| C3H5CH2 | OAc | OCH3 | CH3 |
| C3H5CH2 | OAc | H | CH3 |
| C3H5CH2 | OCH3 | OH | CH3 |
| C3H5CH2 | OCH3 | OAc | CH3 |
| C3H5CH2 | OCH3 | OCH3 | CH3 |
| C3H5CH2 | OCH3 | H | CH3 |
| CH3 | OH | OH | CH3 |
| CH3 | OH | OAc | CH3 |
| CH3 | OH | OCH3 | CH3 |
| CH3 | OAc | OH | CH3 |
| CH3 | OAc | OAc | CH3 |
| CH3 | OAc | OCH3 | CH3 |
| CH3 | OCH3 | OH | CH3 |
| CH3 | OCH3 | OAc | CH3 |
| CH3 | OCH3 | OCH3 | CH3 |
| CH3 | OH | OH | C2H5 |
| CH3 | OH | OH | n-C3H7 |
| CH3 | OH | OH | i-C3H7 |
| CH3 | OH | OH | n-C4H9 |
| CH3 | OH | OH | i-C4H9 |
| CH2CHCH2 | OH | OH | CH3 |
| CH2CHCH2 | OH | OAc | CH3 |
| CH2CHCH2 | OH | OCH3 | CH3 |
| CH2CHCH2 | OAc | OH | CH3 |
| CH2CHCH2 | OAc | OAc | CH3 |
| CH2CHCH2 | OAc | OCH3 | CH3 |
| CH2CHCH2 | OCH3 | OH | CH3 |
| CH2CHCH2 | OCH3 | OAc | CH3 |
| CH2CHCH2 | OCH3 | OCH3 | CH3 |
| CH2CHCH2 | OH | OH | C2H5 |
| CH2CHCH2 | OH | OH | n-C3H7 |
| CH2CHCH2 | OH | OH | i-C3H7 |
| CH2CHCH2 | OH | OH | n-C4H9 |
| CH2CHCH2 | OH | OH | i-C4H9 |
| PhCH2CH2 | OH | OH | CH3 |
| PhCH2CH2 | OH | OAc | CH3 |
| PhCH2CH2 | OH | OCH3 | CH3 |
| PhCH2CH2 | OAc | OH | CH3 |
| PhCH2CH2 | OAc | OAc | CH3 |
| PhCH2CH2 | OAc | OCH3 | CH3 |
| PhCH2CH2 | OCH3 | OH | CH3 |
| PhCH2CH2 | OCH3 | OAc | CH3 |
| PhCH2CH2 | OCH3 | OCH3 | CH3 |
| PhCH2CH2 | OH | OH | C2H5 |
| PhCH2CH2 | OH | OH | n-C3H7 |
| PhCH2CH2 | OH | OH | i-C3H7 |
| PhCH2CH2 | OH | OH | n-C4H9 |
| PhCH2CH2 | OH | OH | i-C4H9 |

The compounds of this invention represented by General formula (II) can be obtained, to put it specifically, by the following method.

Generally, as shown by Chart I, obtainment of the compounds can be achieved by the steps of treating tertiary amine at 17 position of the starting material represented by general formula (VIII) (where $R^1$, $R^2$, $R^3$, $R^4$, $R^5$ and A represent the same as defined in general formula (II)) with an alkylating agent such as halogenated alkyl and methanesulfonate ester, to convert it into a quaternary ammonium salt

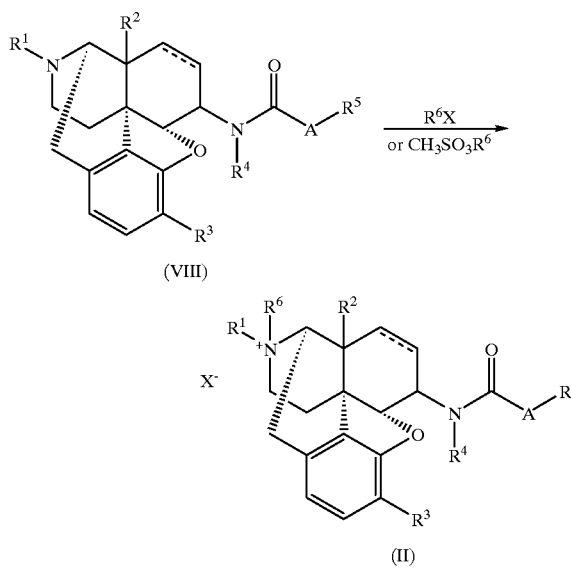

[Chart I]

(VIII)

(II)

The starting material including tertiary amine at 17 position represented by general formula (VIII) can be produced by the method disclosed in Japanese Patent No. 2525552.

There are many alkylating agents that can be used for converting the starting material as represented by general formula (VIII) into a quaternary ammonium salt. Methyl iodide, ethyl iodide, propyl iodide, butyl iodide, allyl iodide, methyl methanesulfonate and dimethyl sulfate e are convenient because they react comparatively rapidly to produce quaternary ammonium salts. However, other alkylating agents such as methyl bromide, ethyl bromide, propyl bromide, butyl bromide, allyl bromide, methyl chloride, ethyl chloride, propyl chloride, butyl chloride and allyl chloride may be also used. As the solvent, ethylene chloride, chloroform, tetrahydrofuran, ethyl acetate, dimethylformamide, acetonitrile, methanol, ethanol, propanol, tertiary buthanol or acetone may be used alone or in combination to serve as the reaction solvent. The reaction temperature is preferably set at 0° C. to the boiling point of solvent, or more preferably at room temperature to the boiling point of solvent; the period is preferably set at 1 to 14 days, or more preferably at 1 to 10 days; and the reaction should proceed in a sealed tube or under a normal pressure. The aforementioned alkylating agent may be added by one equivalent with respect to one equivalent of tertiary amine, or it may be further added, for example, 0.1–5.0 excess equivalents or more excess to amine. Further, potassium hydrogen carbonate, sodium hydrogen carbonate, potassium carbonate or sodium carbonate may be added as a base. One equivalent with respect to one equivalent of tertiary amine, or additional 0.1–5.0 excess equivalents or more excess of the base may be used.

Further, the compounds represented by general formula (III) are new morphinan N-oxide derivatives at 17 position, and opiate κ receptor agonists. In that formula, $R^1$ is preferably alkyl having 1 to 5 carbon atoms, cycloalkylalkyl having 4 to 7 carbon atoms, cycloalkenylalkyl having 5 to 7 carbons, aralkyl having 7 to 13 carbon atoms, alkenyl having 4 to 7 carbon atoms, or allyl; and particularly methyl, ethyl, propyl, butyl, isobutyl, cyclopropylmethyl, cyclobutylmethyl, cyclopentylmethyl, cyclopentenylmethyl, cyolohexenylmethyl, benzyl, phenethyl, trans-2-butenyl, 2-methyl-2-butenyl, or allyl is preferred. More preferred is methyl, ethyl, propyl, butyl, isobutyl, cyclopropylmethy, benzyl, phenethyl or allyl.

$R^2$ is preferably hydrogen, hydroxy, nitro, acetoxy, methoxy, methyl, ethyl or propyl; and particularly hydrogen, hydroxy, acetoxy or methoxy is preferred.

$R^3$ is preferably hydrogen, hydroxy, acetoxy or methoxy.

$R^4$ is preferably hydrogen, straight or branched alkyl having 1 to 5 carbon atoms or phenyl; and particularly straight or branched alkyl having 1 to 5 carbon atoms is preferred. Of them, methyl, ethyl, propyl, isopropyl, butyl or isobutyl is more preferred.

"A" is preferably alkylene having 1 to 6 carbon atoms, —CH=CH—, or —C≡C—; and of them —CH=CH— or —C≡C— is more preferred.

$R^5$ is preferably an organic group having any one of the following basic skeletons:

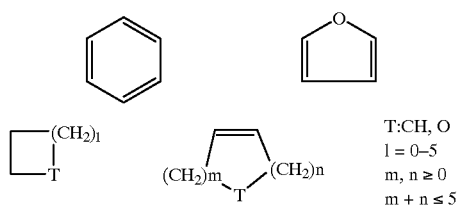

T:CH, O
l = 0–5
m, n ≥ 0
m + n ≤ 5 where the organic group may have its component substituted by at least one substituent selected from the group consisting of alkyl having 1 to 5 carbon atoms, alkoxy having 1 to 5 carbon atoms, alkanoyloxy having 1 to 5 carbon atoms, hydroxy, fluorine, chlorine, bromine, iodine, nitro, cyano, isothiocyanato, trifluoromethyl, trifluoromethoxy and methylenedioxy; a nd particularly phenyl, 2-chlorophenyl, 3-chlorophenyl, 4-chlorophenyl, 3,4-dichlorophenyl, 2-fluorophenyl, 3-fluoro phenyl, 4-fluorophenyl, 3,4-difluorophenyl, 2-bromophenyl, 3-bromophenyl, 4-bromophenyl, 2-nitrophenyl, 3-nitrophenyl, 4-nitrophenyl, 2-trifluoromethylphenyl, 3-trifluoromethylphenyl, 4-trifluoromethylphenyl, 2-trifluoromethoxyphenyl, 3-trifluoromethoxyphenyl, 4-trifluoromethoxyphenyl, 2-methylphenyl, 3-methylphenyl, 4-methylphenyl, 2-meth oxyphenyl, 3-methoxyphenyl, 4-methoxyphenyl, 2-furanyl, 3-furanyl, cyclopentyl, or cyclohexyl is preferred, but what is preferred should not be limited to them.

Concrete examples of the compounds as represented by general formula (III) are shown in Table 2. The compounds represented by general formula (III) comprise (+), (−) and (±) isomers.

TABLE 2

| R1 | R2 | R3 | R4 |
|---|---|---|---|

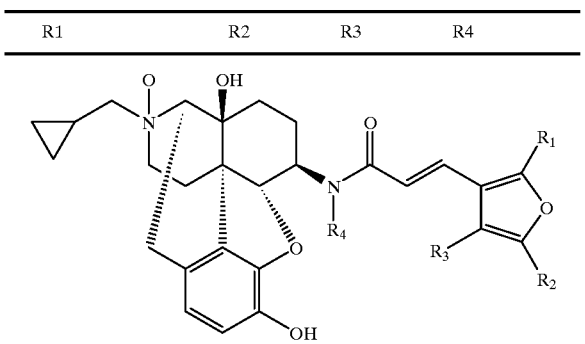

| H | H | H | CH3 |
| H | H | H | C2H5 |
| H | H | H | n-C3H7 |
| H | H | H | i-C3H7 |
| H | H | H | n-C4H9 |
| H | H | H | i-C4H9 |
| CH3 | H | H | CH3 |
| H | CH3 | H | CH3 |
| H | H | CH3 | CH3 |
| CH3 | H | H | C2H5 |
| Cl | H | H | CH3 |
| H | Cl | H | CH3 |
| H | H | Cl | CH3 |
| H | Cl | H | C2H5 |
| Br | H | H | CH3 |
| H | Br | H | CH3 |
| H | H | Br | CH3 |
| H | Br | H | C2H5 |
| F | H | H | CH3 |
| H | F | H | CH3 |
| H | H | F | CH3 |
| H | F | H | C2H5 |
| CF3 | H | H | CH3 |
| H | CF3 | H | CH3 |
| H | H | CF3 | CH3 |
| CF3 | H | H | C2H5 |
| CN | H | H | CH3 |
| H | CN | H | CH3 |
| H | H | CN | CH3 |
| CN | H | H | C2H5 |

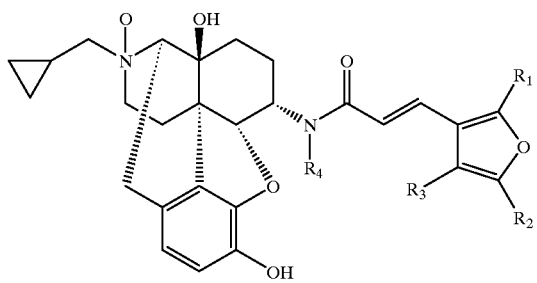

| H | H | H | CH3 |
| H | H | H | C2H5 |
| H | H | H | n-C3H7 |
| H | H | H | i-C3H7 |
| H | H | H | n-C4H9 |
| H | H | H | i-C4H9 |
| CH3 | H | H | CH3 |
| H | CH3 | H | CH3 |
| H | H | CH3 | CH3 |
| CH3 | H | H | C2H5 |
| Cl | H | H | CH3 |
| H | Cl | H | CH3 |
| H | H | Cl | CH3 |
| H | Cl | H | C2H5 |
| Br | H | H | CH3 |
| H | Br | H | CH3 |
| H | H | Br | CH3 |
| H | Br | H | C2H5 |
| F | H | H | CH3 |
| H | F | H | CH3 |
| H | H | F | CH3 |
| H | F | H | C2H5 |
| CF3 | H | H | CH3 |
| H | CF3 | H | CH3 |
| H | H | CF3 | CH3 |
| CF3 | H | H | C2H5 |
| CN | H | H | CH3 |
| H | CN | H | CH3 |
| H | H | CN | CH3 |
| CN | H | H | C2H5 |

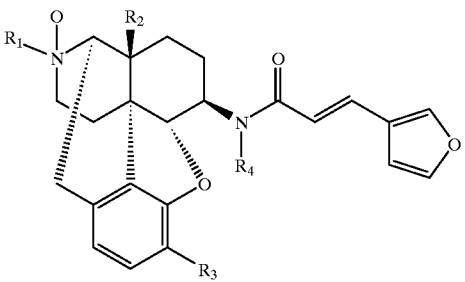

| C3H5CH2 | OH | OAc | CH3 |
| C3H5CH2 | OH | OCH3 | CH3 |
| C3H5CH2 | OH | H | CH3 |
| C3H5CH2 | OAc | OH | CH3 |
| C3H5CH2 | OAc | OAc | CH3 |
| C3H5CH2 | OAc | OCH3 | CH3 |
| C3H5CH2 | OAc | H | CH3 |
| C3H5CH2 | OCH3 | OH | CH3 |
| C3H5CH2 | OCH3 | OAc | CH3 |
| C3H5CH2 | OCH3 | OCH3 | CH3 |
| C3H5CH2 | OCH3 | H | CH3 |
| C3H5CH2 | OH | OAc | C2H5 |
| C3H5CH2 | OH | OAc | n-C3H7 |
| C3H5CH2 | OH | OAc | i-C3H5 |
| C3H5CH2 | OH | OCH3 | C2H5 |
| C3H5CH2 | OH | OCH3 | n-C3H7 |
| CH3 | OH | OH | CH3 |
| CH3 | OH | OAc | CH3 |
| CH3 | OH | OCH3 | CH3 |
| CH3 | OAc | OH | CH3 |
| CH3 | OAc | OAc | CH3 |
| CH3 | OAc | OCH3 | CH3 |
| CH3 | OCH3 | OH | CH3 |
| CH3 | OCH3 | OAc | CH3 |
| CH3 | OCH3 | OCH3 | CH3 |
| CH3 | OH | OH | C2H5 |
| CH3 | OH | OH | n-C3H7 |
| CH3 | OH | OH | i-C3H7 |
| CH3 | OH | OH | n-C4H9 |
| CH3 | OH | OH | i-C4H9 |
| CH3 | OH | OAc | C2H5 |
| CH2CHCH2 | OH | OH | CH3 |
| CH2CHCH2 | OH | OAc | CH3 |
| CH2CHCH2 | OH | OCH3 | CH3 |
| CH2CHCH2 | OAc | OH | CH3 |
| CH2CHCH2 | OAc | OAc | CH3 |
| CH2CHCH2 | OAc | OCH3 | CH3 |
| CH2CHCH2 | OCH3 | OH | CH3 |
| CH2CHCH2 | OCH3 | OAc | CH3 |
| CH2CHCH2 | OCH3 | OCH3 | CH3 |
| CH2CHCH2 | OH | OH | C2H5 |
| CH2CHCH2 | OH | OH | n-C3H7 |
| CH2CHCH2 | OH | OH | i-C3H7 |
| CH2CHCH2 | OH | OH | n-C4H9 |
| CH2CHCH2 | OH | OH | i-C4H9 |
| CH2CHCH2 | OH | OAc | C2H5 |
| PhCH2CH2 | OH | OH | CH3 |
| PhCH2CH2 | OH | OAc | CH3 |
| PhCH2CH2 | OH | OCH3 | CH3 |
| PhCH2CH2 | OAc | OH | CH3 |

TABLE 2-continued

| | | | |
|---|---|---|---|
| PhCH2CH2 | OAc | OAc | CH3 |
| PhCH2CH2 | OAc | OCH3 | CH3 |
| PhCH2CH2 | OCH3 | OH | CH3 |
| PhCH2CH2 | OCH3 | OAc | CH3 |
| PhCH2CH2 | OCH3 | OCH3 | CH3 |
| PhCH2CH2 | OH | OH | C2H5 |
| PhCH2CH2 | OH | OH | n-C3H7 |
| PhCH2CH2 | OH | OH | i-C3H7 |
| PhCH2CH2 | OH | OH | n-C4H9 |
| PhCH2CH2 | OH | OH | i-C4H9 |
| PhCH2CH2 | OH | OAc | C2H5 |

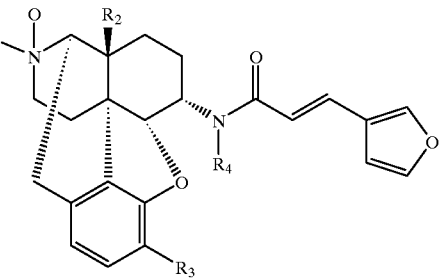

| | | | |
|---|---|---|---|
| C3H5CH2 | OH | OAc | CH3 |
| C3H5CH2 | OH | OCH3 | CH3 |
| C3H5CH2 | OH | H | CH3 |
| C3H5CH2 | OAc | OH | CH3 |
| C3H5CH2 | OAc | OAc | CH3 |
| C3H5CH2 | OAc | OCH3 | CH3 |
| C3H5CH2 | OAc | H | CH3 |
| C3H5CH2 | OCH3 | OH | CH3 |
| C3H5CH2 | OCH3 | OAc | CH3 |
| C3H5CH2 | OCH3 | OCH3 | CH3 |
| C3H5CH2 | OCH3 | H | CH3 |
| C3H5CH2 | OH | OAc | C2H5 |
| C3H5CH2 | OH | OAc | n-C3H7 |
| C3H5CH2 | OH | OAc | i-C3H5 |
| C3H5CH2 | OH | OCH3 | C2H5 |
| C3H5CH2 | OH | OCH3 | n-C3H7 |
| CH3 | OH | OH | CH3 |
| CH3 | OH | OAc | CH3 |
| CH3 | OH | OCH3 | CH3 |
| CH3 | OAc | OH | CH3 |
| CH3 | OAc | OAc | CH3 |
| CH3 | OAc | OCH3 | CH3 |
| CH3 | OCH3 | OH | CH3 |
| CH3 | OCH3 | OAc | CH3 |
| CH3 | OCH3 | OCH3 | CH3 |
| CH3 | OH | OH | C2H5 |
| CH3 | OH | OH | n-C3H7 |
| CH3 | OH | OH | i-C3H7 |
| CH3 | OH | OH | n-C4H9 |
| CH3 | OH | OH | i-C4H9 |
| CH3 | OH | OAc | C2H5 |
| CH2CHCH2 | OH | OH | CH3 |
| CH2CHCH2 | OH | OAc | CH3 |
| CH2CHCH2 | OH | OCH3 | CH3 |
| CH2CHCH2 | OAc | OH | CH3 |
| CH2CHCH2 | OAc | OAc | CH3 |
| CH2CHCH2 | OAc | OCH3 | CH3 |
| CH2CHCH2 | OCH3 | OH | CH3 |
| CH2CHCH2 | OCH3 | OAc | CH3 |
| CH2CHCH2 | OCH3 | OCH3 | CH3 |
| CH2CHCH2 | OH | OH | C2H5 |
| CH2CHCH2 | OH | OH | n-C3H7 |
| CH2CHCH2 | OH | OH | i-C3H7 |
| CH2CHCH2 | OH | OH | n-C4H9 |
| CH2CHCH2 | OH | OH | i-C4H9 |
| CH2CHCH2 | OH | OAc | C2H5 |
| PhCH2CH2 | OH | OH | CH3 |
| PhCH2CH2 | OH | OAc | CH3 |
| PhCH2CH2 | OH | OCH3 | CH3 |
| PhCH2CH2 | OAc | OH | CH3 |
| PhCH2CH2 | OAc | OAc | CH3 |
| PhCH2CH2 | OAc | OCH3 | CH3 |
| PhCH2CH2 | OCH3 | OH | CH3 |
| PhCH2CH2 | OCH3 | OAc | CH3 |
| PhCH2CH2 | OCH3 | OCH3 | CH3 |
| PhCH2CH2 | OH | OH | C2H5 |
| PhCH2CH2 | OH | OH | n-C3H7 |
| PhCH2CH2 | OH | OH | i-C3H7 |
| PhCH2CH2 | OH | OH | n-C4H9 |
| PhCH2CH2 | OH | OH | i-C4H9 |
| PhCH2CH2 | OH | OAc | C2H5 |

| | | | |
|---|---|---|---|
| H | H | H | CH3 |
| H | H | H | C2H5 |
| H | H | H | n-C3H7 |
| H | H | H | i-C3H7 |
| H | H | H | n-C4H9 |
| H | H | H | i-C4H9 |
| CH3 | H | H | CH3 |
| H | CH3 | H | CH3 |
| H | H | CH3 | CH3 |
| CH3 | H | H | C2H5 |
| Cl | H | H | CH3 |
| H | Cl | H | CH3 |
| H | H | Cl | CH3 |
| Cl | H | H | C2H5 |
| Br | H | H | CH3 |
| H | Br | H | CH3 |
| H | H | Br | CH3 |
| Br | H | H | C2H5 |
| F | H | H | CH3 |
| H | F | H | CH3 |
| H | H | F | CH3 |
| F | H | H | C2H5 |
| CF3 | H | H | CH3 |
| H | CF3 | H | CH3 |
| H | H | CF3 | CH3 |
| CF3 | H | H | C2H5 |
| CN | H | H | CH3 |
| H | CN | H | CH3 |
| H | H | CN | CH3 |
| CN | H | H | C2H5 |

| | | | |
|---|---|---|---|
| H | H | H | CH3 |
| H | H | H | C2H5 |
| H | H | H | n-C3H7 |
| H | H | H | i-C3H7 |
| H | H | H | n-C4H9 |
| H | H | H | i-C4H9 |
| CH3 | H | H | CH3 |
| H | CH3 | H | CH3 |
| H | H | CH3 | CH3 |

TABLE 2-continued

| | | | |
|---|---|---|---|
| CH3 | H | H | C2H5 |
| Cl | H | H | CH3 |
| H | Cl | H | CH3 |
| H | H | Cl | CH3 |
| Cl | H | H | C2H5 |
| Br | H | H | CH3 |
| H | Br | H | CH3 |
| H | H | Br | CH3 |
| Br | H | H | C2H5 |
| F | H | H | CH3 |
| H | F | H | CH3 |
| H | H | F | CH3 |
| F | H | H | C2H5 |
| CF3 | H | H | CH3 |
| H | CF3 | H | CH3 |
| H | H | CF3 | CH3 |
| CF3 | H | H | C2H5 |
| CN | H | H | CH3 |
| H | CN | H | CH3 |
| H | H | CN | CH3 |
| CN | H | H | C2H5 |

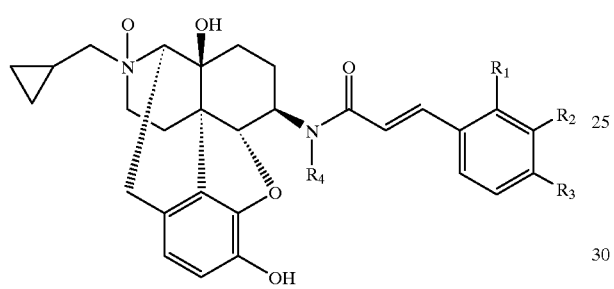

| | | | |
|---|---|---|---|
| H | H | H | CH3 |
| H | H | H | C2H5 |
| CH3 | H | H | CH3 |
| H | CH3 | H | CH3 |
| H | H | CH3 | CH3 |
| H | CH3 | CH3 | CH3 |
| H | CH3 | H | C2H5 |
| H | CH3 | H | n-C3H7 |
| H | CH3 | H | i-C3H7 |
| H | CH3 | H | n-C4H9 |
| H | CH3 | H | i-C4H9 |
| OCH3 | H | H | CH3 |
| H | OCH3 | H | CH3 |
| H | H | OCH3 | CH3 |
| H | OCH3 | OCH3 | CH3 |
| H | OCH3 | H | C2H5 |
| H | OCH3 | H | n-C3H7 |
| H | OCH3 | H | i-C3H7 |
| H | OCH3 | H | n-C4H9 |
| H | OCH3 | H | i-C4H9 |
| OH | H | H | CH3 |
| H | OH | H | CH3 |
| H | H | OH | CH3 |
| Cl | H | H | CH3 |
| H | Cl | H | CH3 |
| H | H | Cl | CH3 |
| H | Cl | Cl | CH3 |
| H | Cl | Cl | C2H5 |
| H | Cl | Cl | n-C3H7 |
| H | Cl | Cl | n-C4H9 |
| Br | H | H | CH3 |
| H | Br | H | CH3 |
| H | H | Br | CH3 |
| H | Br | Br | CH3 |
| H | Br | Br | C2H5 |
| F | H | H | CH3 |
| H | F | H | CH3 |
| H | H | F | CH3 |
| H | F | F | CH3 |
| H | F | F | C2H5 |
| NO2 | H | H | CH3 |
| H | NO2 | H | CH3 |

TABLE 2-continued

| | | | |
|---|---|---|---|
| H | H | NO2 | CH3 |
| CF3 | H | H | CH3 |
| H | CF3 | H | CH3 |
| H | H | CF3 | CH3 |
| H | H | CF3 | C2H5 |
| H | H | CF3 | n-C3H7 |
| H | H | CH3 | i-C3H7 |
| H | H | CF3 | n-C4H9 |
| H | H | CF3 | i-C4H9 |
| OCF3 | H | H | CH3 |
| H | OCF3 | H | CH3 |
| H | H | OCF3 | CH3 |
| H | OCF3 | H | C2H5 |
| H | OCF3 | H | n-C3H7 |
| H | OCF3 | H | i-C3H7 |
| H | OCF3 | H | n-C4H9 |
| H | OCF3 | H | i-C4H9 |

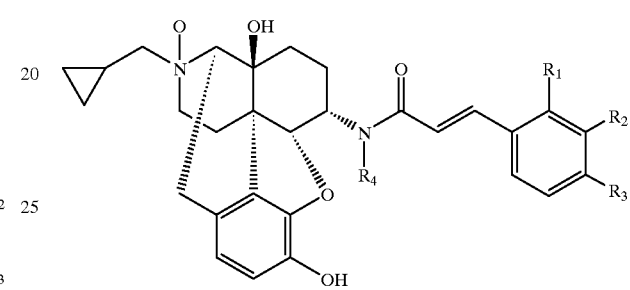

| | | | |
|---|---|---|---|
| H | H | H | CH3 |
| H | H | H | C2H5 |
| CH3 | H | H | CH3 |
| H | CH3 | H | CH3 |
| H | H | CH3 | CH3 |
| H | CH3 | CH3 | CH3 |
| H | CH3 | H | C2H5 |
| H | CH3 | H | n-C3H7 |
| H | CH3 | H | i-C3H7 |
| H | CH3 | H | n-C4H9 |
| H | CH3 | H | i-C4H9 |
| OCH3 | H | H | CH3 |
| H | OCH3 | H | CH3 |
| H | H | OCH3 | CH3 |
| H | OCH3 | OCH3 | CH3 |
| H | OCH3 | H | C2H5 |
| H | OCH3 | H | n-C3H7 |
| H | OCH3 | H | i-C3H7 |
| H | OCH3 | H | n-C4H9 |
| H | OCH3 | H | i-C4H9 |
| OH | H | H | CH3 |
| H | OH | H | CH3 |
| H | H | OH | CH3 |
| Cl | H | H | CH3 |
| H | Cl | H | CH3 |
| H | H | Cl | CH3 |
| H | Cl | Cl | CH3 |
| H | Cl | Cl | C2H5 |
| H | Cl | Cl | n-C3H7 |
| H | Cl | Cl | n-C4H9 |
| Br | H | H | CH3 |
| H | Br | H | CH3 |
| H | H | Br | CH3 |
| H | Br | Br | CH3 |
| H | Br | Br | C2H5 |
| F | H | H | CH3 |
| H | F | H | CH3 |
| H | H | F | CH3 |
| H | F | F | CH3 |
| H | F | F | C2H5 |
| NO2 | H | H | CH3 |
| H | NO2 | H | CH3 |
| H | H | NO2 | CH3 |
| CF3 | H | H | CH3 |
| H | CF3 | H | CH3 |
| H | H | CF3 | CH3 |

TABLE 2-continued

| | | | |
|---|---|---|---|
| H | H | CF3 | C2H5 |
| H | H | CF3 | n-C3H7 |
| H | H | CH3 | i-C3H7 |
| H | H | CF3 | n-C4H9 |
| H | H | CF3 | i-C4H9 |
| OCF3 | H | H | CH3 |
| H | OCF3 | H | CH3 |
| H | H | OCF3 | CH3 |
| H | OCF3 | H | C2H5 |
| H | OCF3 | H | n-C3H7 |
| H | OCF3 | H | i-C3H7 |
| H | OCF3 | H | n-C4H9 |
| H | OCF3 | H | i-C4H9 |

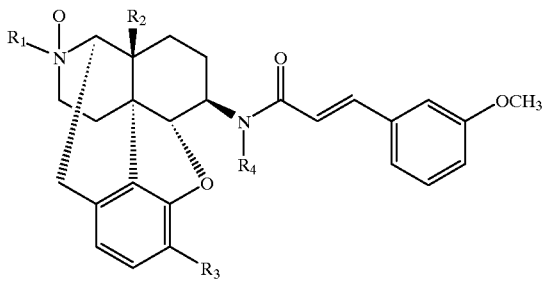

| | | | |
|---|---|---|---|
| C3H5CH2 | OH | OAc | CH3 |
| C3H5CH2 | OH | OCH3 | CH3 |
| C3H5CH2 | OH | H | CH3 |
| C3H5CH2 | OAc | OH | CH3 |
| C3H5CH2 | OAc | OAc | CH3 |
| C3H5CH2 | OAc | OCH3 | CH3 |
| C3H5CH2 | OAc | H | CH3 |
| C3H5CH2 | OCH3 | OH | CH3 |
| C3H5CH2 | OCH3 | OAc | CH3 |
| C3H5CH2 | OCH3 | OCH3 | CH3 |
| C3H5CH2 | OCH3 | H | CH3 |
| C3H5CH2 | OH | OAc | C2H5 |
| C3H5CH2 | OH | OAc | n-C3H7 |
| C3H5CH2 | OH | OAc | i-C3H5 |
| C3H5CH2 | OH | OCH3 | C2H5 |
| C3H5CH2 | OH | OCH3 | n-C3H7 |
| CH3 | OH | OH | CH3 |
| CH3 | OH | OAc | CH3 |
| CH3 | OH | OCH3 | CH3 |
| CH3 | OAc | OH | CH3 |
| CH3 | OAc | OAc | CH3 |
| CH3 | OAc | OCH3 | CH3 |
| CH3 | OCH3 | OH | CH3 |
| CH3 | OCH3 | OAc | CH3 |
| CH3 | OCH3 | OCH3 | CH3 |
| CH3 | OH | OH | C2H5 |
| CH3 | OH | OH | n-C3H7 |
| CH3 | OH | OH | i-C3H7 |
| CH3 | OH | OH | n-C4H9 |
| CH3 | OH | OH | i-C4H9 |
| CH3 | OH | OAc | C2H5 |
| CH2CHCH2 | OH | OH | CH3 |
| CH2CHCH2 | OH | OAc | CH3 |
| CH2CHCH2 | OH | OCH3 | CH3 |
| CH2CHCH2 | OAc | OH | CH3 |
| CH2CHCH2 | OAc | OAc | CH3 |
| CH2CHCH2 | OAc | OCH3 | CH3 |
| CH2CHCH2 | OCH3 | OH | CH3 |
| CH2CHCH2 | OCH3 | OAc | CH3 |
| CH2CHCH2 | OCH3 | OCH3 | CH3 |
| CH2CHCH2 | OH | OH | C2H5 |
| CH2CHCH2 | OH | OH | n-C3H7 |
| CH2CHCH2 | OH | OH | i-C3H7 |
| CH2CHCH2 | OH | OH | n-C4H9 |
| CH2CHCH2 | OH | OH | i-C4H9 |
| CH2CHCH2 | OH | OAc | C2H5 |
| PhCH2CH2 | OH | OH | CH3 |
| PhCH2CH2 | OH | OAc | CH3 |
| PhCH2CH2 | OH | OCH3 | CH3 |
| PhCH2CH2 | OAc | OH | CH3 |

TABLE 2-continued

| | | | |
|---|---|---|---|
| PhCH2CH2 | OAc | OAc | CH3 |
| PhCH2CH2 | OAc | OCH3 | CH3 |
| PhCH2CH2 | OCH3 | OH | CH3 |
| PhCH2CH2 | OCH3 | OAc | CH3 |
| PhCH2CH2 | OCH3 | OCH3 | CH3 |
| PhCH2CH2 | OH | OH | C2H5 |
| PhCH2CH2 | OH | OH | n-C3H7 |
| PhCH2CH2 | OH | OH | i-C3H7 |
| PhCH2CH2 | OH | OH | n-C4H9 |
| PhCH2CH2 | OH | OH | i-C4H9 |
| PhCH2CH2 | OH | OAc | C2H5 |

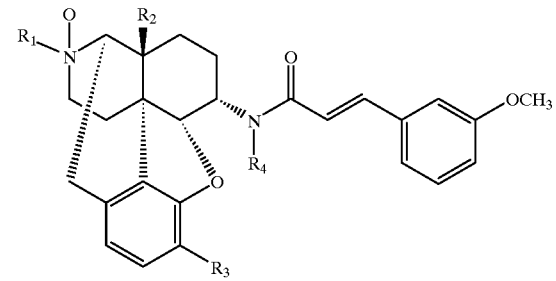

| | | | |
|---|---|---|---|
| C3H5CH2 | OH | OAc | CH3 |
| C3H5CH2 | OH | OCH3 | CH3 |
| C3H5CH2 | OH | H | CH3 |
| C3H5CH2 | OAc | OH | CH3 |
| C3H5CH2 | OAc | OAc | CH3 |
| C3H5CH2 | OAc | OCH3 | CH3 |
| C3H5CH2 | OAc | H | CH3 |
| C3H5CH2 | OCH3 | OH | CH3 |
| C3H5CH2 | OCH3 | OAc | CH3 |
| C3H5CH2 | OCH3 | OCH3 | CH3 |
| C3H5CH2 | OCH3 | H | CH3 |
| C3H5CH2 | OH | OAc | C2H5 |
| C3H5CH2 | OH | OAc | n-C3H7 |
| C3H5CH2 | OH | OAc | i-C3H5 |
| C3H5CH2 | OH | OCH3 | C2H5 |
| C3H5CH2 | OH | OCH3 | n-C3H7 |
| CH3 | OH | OH | CH3 |
| CH3 | OH | OAc | CH3 |
| CH3 | OH | OCH3 | CH3 |
| CH3 | OAc | OH | CH3 |
| CH3 | OAc | OAc | CH3 |
| CH3 | OAc | OCH3 | CH3 |
| CH3 | OCH3 | OH | CH3 |
| CH3 | OCH3 | OAc | CH3 |
| CH3 | OCH3 | OCH3 | CH3 |
| CH3 | OH | OH | C2H5 |
| CH3 | OH | OH | n-C3H7 |
| CH3 | OH | OH | i-C3H7 |
| CH3 | OH | OH | n-C4H9 |
| CH3 | OH | OH | i-C4H9 |
| CH3 | OH | OAc | C2H5 |
| CH2CHCH2 | OH | OH | CH3 |
| CH2CHCH2 | OH | OAc | CH3 |
| CH2CHCH2 | OH | OCH3 | CH3 |
| CH2CHCH2 | OAc | OH | CH3 |
| CH2CHCH2 | OAc | OAc | CH3 |
| CH2CHCH2 | OAc | OCH3 | CH3 |
| CH2CHCH2 | OCH3 | OH | CH3 |
| CH2CHCH2 | OCH3 | OAc | CH3 |
| CH2CHCH2 | OCH3 | OCH3 | CH3 |
| CH2CHCH2 | OH | OH | C2H5 |
| CH2CHCH2 | OH | OH | n-C3H7 |
| CH2CHCH2 | OH | OH | i-C3H7 |
| CH2CHCH2 | OH | OH | n-C4H9 |
| CH2CHCH2 | OH | OH | i-C4H9 |
| CH2CHCH2 | OH | OAc | C2H5 |
| PhCH2CH2 | OH | OH | CH3 |
| PhCH2CH2 | OH | OAc | CH3 |
| PhCH2CH2 | OH | OCH3 | CH3 |
| PhCH2CH2 | OAc | OH | CH3 |
| PhCH2CH2 | OAc | OAc | CH3 |
| PhCH2CH2 | OAc | OCH3 | CH3 |

TABLE 2-continued

| | | | |
|---|---|---|---|
| PhCH2CH2 | OCH3 | OH | CH3 |
| PhCH2CH2 | OCH3 | OAc | CH3 |
| PhCH2CH2 | OCH3 | OCH3 | CH3 |
| PhCH2CH2 | OH | OH | C2H5 |
| PhCH2CH2 | OH | OH | n-C3H7 |
| PhCH2CH2 | OH | OH | i-C3H7 |
| PhCH2CH2 | OH | OH | n-C4H9 |
| PhCH2CH2 | OH | OH | i-C4H9 |
| PhCH2CH2 | OH | OAc | C2H5 |

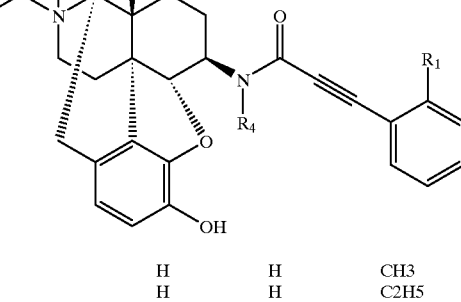

| | | | |
|---|---|---|---|
| H | H | H | CH3 |
| H | H | H | C2H5 |
| CH3 | H | H | CH3 |
| H | CH3 | H | CH3 |
| H | H | CH3 | CH3 |
| H | CH3 | CH3 | CH3 |
| H | CH3 | H | C2H5 |
| H | CH3 | H | n-C3H7 |
| H | CH3 | H | i-C3H7 |
| H | CH3 | H | n-C4H9 |
| H | CH3 | H | i-C4H9 |
| OCH3 | H | H | CH3 |
| H | OCH3 | H | CH3 |
| H | H | OCH3 | CH3 |
| H | OCH3 | OCH3 | CH3 |
| H | OCH3 | H | C2H5 |
| H | OCH3 | H | n-C3H7 |
| H | OCH3 | H | i-C3H7 |
| H | OCH3 | H | n-C4H9 |
| H | OCH3 | H | i-C4H9 |
| OH | H | H | CH3 |
| H | OH | H | CH3 |
| H | H | OH | CH3 |
| Cl | H | H | CH3 |
| H | Cl | H | CH3 |
| H | H | Cl | CH3 |
| H | Cl | Cl | CH3 |
| H | Cl | Cl | C2H5 |
| H | Cl | Cl | n-C3H7 |
| H | Cl | Cl | n-C4H9 |
| Br | H | H | CH3 |
| H | Br | H | CH3 |
| H | H | Br | CH3 |
| H | Br | Br | CH3 |
| H | Br | Br | C2H5 |
| F | H | H | CH3 |
| H | F | H | CH3 |
| H | F | F | CH3 |
| H | F | F | C2H5 |
| NO2 | H | H | CH3 |
| H | NO2 | H | CH3 |
| H | H | NO2 | CH3 |
| CF3 | H | H | CH3 |
| H | CF3 | H | CH3 |
| H | H | CF3 | CH3 |
| H | H | CF3 | C2H5 |
| H | H | CF3 | n-C3H7 |
| H | H | CH3 | i-C3H7 |
| H | H | CF3 | n-C4H9 |
| H | H | CF3 | i-C4H9 |
| OCF3 | H | H | CH3 |
| H | OCF3 | H | CH3 |
| H | H | OCF3 | CH3 |

| | | | |
|---|---|---|---|
| H | OCF3 | H | C2H5 |
| H | OCF3 | H | n-C3H7 |
| H | OCF3 | H | i-C3H7 |
| H | OCF3 | H | n-C4H9 |
| H | OCF3 | H | i-C4H9 |

| | | | |
|---|---|---|---|
| H | H | H | CH3 |
| H | H | H | C2H5 |
| CH3 | H | H | CH3 |
| H | CH3 | H | CH3 |
| H | H | CH3 | CH3 |
| H | CH3 | CH3 | CH3 |
| H | CH3 | H | C2H5 |
| H | CH3 | H | n-C3H7 |
| H | CH3 | H | i-C3H7 |
| H | CH3 | H | n-C4H9 |
| H | CH3 | H | i-C4H9 |
| OCH3 | H | H | CH3 |
| H | OCH3 | H | CH3 |
| H | H | OCH3 | CH3 |
| H | OCH3 | OCH3 | CH3 |
| H | OCH3 | H | C2H5 |
| H | OCH3 | H | n-C3H7 |
| H | OCH3 | H | i-C3H7 |
| H | OCH3 | H | n-C4H9 |
| H | OCH3 | H | i-C4H9 |
| OH | H | H | CH3 |
| H | OH | H | CH3 |
| H | H | OH | CH3 |
| Cl | H | H | CH3 |
| H | Cl | H | CH3 |
| H | H | Cl | CH3 |
| H | Cl | Cl | CH3 |
| H | Cl | Cl | C2H5 |
| H | Cl | Cl | n-C3H7 |
| H | Cl | Cl | n-C4H9 |
| Br | H | H | CH3 |
| H | Br | H | CH3 |
| H | H | Br | CH3 |
| H | Br | Br | CH3 |
| H | Br | Br | C2H5 |
| F | H | H | CH3 |
| H | F | H | CH3 |
| H | H | F | CH3 |
| H | F | F | CH3 |
| H | F | F | C2H5 |
| NO2 | H | H | CH3 |
| H | NO2 | H | CH3 |
| H | H | NO2 | CH3 |
| CF3 | H | H | CH3 |
| H | CF3 | H | CH3 |
| H | H | CF3 | CH3 |
| H | H | CF3 | C2H5 |
| H | H | CF3 | n-C3H7 |
| H | H | CH3 | i-C3H7 |
| H | H | CF3 | n-C4H9 |
| H | H | CF3 | i-C4H9 |
| OCF3 | H | H | CH3 |
| H | OCF3 | H | CH3 |
| H | H | OCF3 | CH3 |
| H | OCF3 | H | C2H5 |
| H | OCF3 | H | n-C3H7 |
| H | OCF3 | H | i-C3H7 |
| H | OCF3 | H | n-C4H9 |
| H | OCF3 | H | i-C4H9 |

TABLE 2-continued

| | | | |
|---|---|---|---|
| H | OCF3 | H | i-C4H9 |

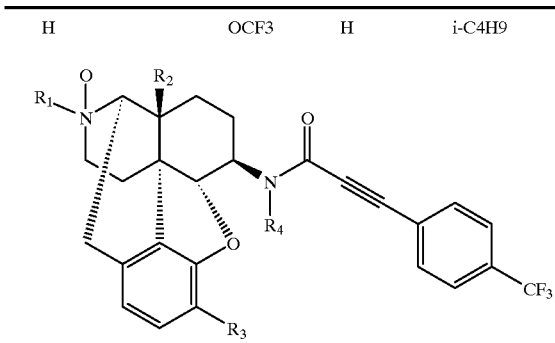

| R1 | R2 | R3 | R4 |
|---|---|---|---|
| C3H5CH2 | OH | OAc | CH3 |
| C3H5CH2 | OH | OCH3 | CH3 |
| C3H5CH2 | OH | H | CH3 |
| C3H5CH2 | OAc | OH | CH3 |
| C3H5CH2 | OAc | OAc | CH3 |
| C3H5CH2 | OAc | OCH3 | CH3 |
| C3H5CH2 | OAc | H | CH3 |
| C3H5CH2 | OCH3 | OH | CH3 |
| C3H5CH2 | OCH3 | OAc | CH3 |
| C3H5CH2 | OCH3 | OCH3 | CH3 |
| C3H5CH2 | OCH3 | H | CH3 |
| C3H5CH2 | OH | OAc | C2H5 |
| C3H5CH2 | OH | OAc | n-C3H7 |
| C3H5CH2 | OH | OAc | i-C3H5 |
| C3H5CH2 | OH | OCH3 | C2H5 |
| C3H5CH2 | OH | OCH3 | n-C3H7 |
| CH3 | OH | OH | CH3 |
| CH3 | OH | OAc | CH3 |
| CH3 | OH | OCH3 | CH3 |
| CH3 | OAc | OH | CH3 |
| CH3 | OAc | OAc | CH3 |
| CH3 | OAc | OCH3 | CH3 |
| CH3 | OCH3 | OH | CH3 |
| CH3 | OCH3 | OAc | CH3 |
| CH3 | OCH3 | OCH3 | CH3 |
| CH3 | OH | OH | C2H5 |
| CH3 | OH | OH | n-C3H7 |
| CH3 | OH | OH | i-C3H7 |
| CH3 | OH | OH | n-C4H9 |
| CH3 | OH | OH | i-C4H9 |
| CH3 | OH | OAc | C2H5 |
| CH2CHCH2 | OH | OH | CH3 |
| CH2CHCH2 | OH | OAc | CH3 |
| CH2CHCH2 | OH | OCH3 | CH3 |
| CH2CHCH2 | OAc | OH | CH3 |
| CH2CHCH2 | OAc | OAc | CH3 |
| CH2CHCH2 | OAc | OCH3 | CH3 |
| CH2CHCH2 | OCH3 | OH | CH3 |
| CH2CHCH2 | OCH3 | OAc | CH3 |
| CH2CHCH2 | OCH3 | OCH3 | CH3 |
| CH2CHCH2 | OH | OH | C2H5 |
| CH2CHCH2 | OH | OH | n-C3H7 |
| CH2CHCH2 | OH | OH | i-C3H7 |
| CH2CHCH2 | OH | OH | n-C4H9 |
| CH2CHCH2 | OH | OH | i-C4H9 |
| CH2CHCH2 | OH | OAc | C2H5 |
| PhCH2CH2 | OH | OH | CH3 |
| PhCH2CH2 | OH | OAc | CH3 |
| PhCH2CH2 | OH | OCH3 | CH3 |
| PhCH2CH2 | OAc | OH | CH3 |
| PhCH2CH2 | OAc | OAc | CH3 |
| PhCH2CH2 | OAc | OCH3 | CH3 |
| PhCH2CH2 | OCH3 | OH | CH3 |
| PhCH2CH2 | OCH3 | OAc | CH3 |
| PhCH2CH2 | OCH3 | OCH3 | CH3 |
| PhCH2CH2 | OH | OH | C2H5 |
| PhCH2CH2 | OH | OH | n-C3H7 |
| PhCH2CH2 | OH | OH | i-C3H7 |
| PhCH2CH2 | OH | OH | n-C4H9 |
| PhCH2CH2 | OH | OH | i-C4H9 |
| PhCH2CH2 | OH | OAc | C2H5 |

TABLE 2-continued

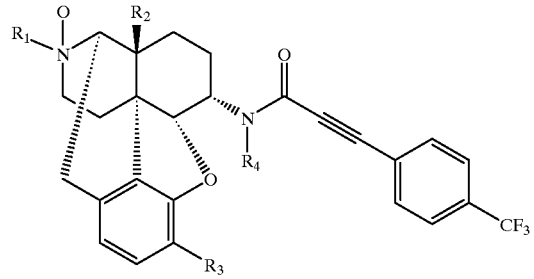

| R1 | R2 | R3 | R4 |
|---|---|---|---|
| C3H5CH2 | OH | OAc | CH3 |
| C3H5CH2 | OH | OCH3 | CH3 |
| C3H5CH2 | OH | H | CH3 |
| C3H5CH2 | OAc | OH | CH3 |
| C3H5CH2 | OAc | OAc | CH3 |
| C3H5CH2 | OAc | OCH3 | CH3 |
| C3H5CH2 | OAc | H | CH3 |
| C3H5CH2 | OCH3 | OH | CH3 |
| C3H5CH2 | OCH3 | OAc | CH3 |
| C3H5CH2 | OCH3 | OCH3 | CH3 |
| C3H5CH2 | OCH3 | H | CH3 |
| C3H5CH2 | OH | OAc | C2H5 |
| C3H5CH2 | OH | OAc | n-C3H7 |
| C3H5CH2 | OH | OAc | i-C3H5 |
| C3H5CH2 | OH | OCH3 | C2H5 |
| C3H5CH2 | OH | OCH3 | n-C3H7 |
| CH3 | OH | OH | CH3 |
| CH3 | OH | OAc | CH3 |
| CH3 | OH | OCH3 | CH3 |
| CH3 | OAc | OH | CH3 |
| CH3 | OAc | OAc | CH3 |
| CH3 | OAc | OCH3 | CH3 |
| CH3 | OCH3 | OH | CH3 |
| CH3 | OCH3 | OAc | CH3 |
| CH3 | OCH3 | OCH3 | CH3 |
| CH3 | OH | OH | C2H5 |
| CH3 | OH | OH | n-C3H7 |
| CH3 | OH | OH | i-C3H7 |
| CH3 | OH | OH | n-C4H9 |
| CH3 | OH | OH | i-C4H9 |
| CH3 | OH | OAc | C2H5 |
| CH2CHCH2 | OH | OH | CH3 |
| CH2CHCH2 | OH | OAc | CH3 |
| CH2CHCH2 | OH | OCH3 | CH3 |
| CH2CHCH2 | OAc | OH | CH3 |
| CH2CHCH2 | OAc | OAc | CH3 |
| CH2CHCH2 | OAc | OCH3 | CH3 |
| CH2CHCH2 | OCH3 | OH | CH3 |
| CH2CHCH2 | OCH3 | OAc | CH3 |
| CH2CHCH2 | OCH3 | OCH3 | CH3 |
| CH2CHCH2 | OH | OH | C2H5 |
| CH2CHCH2 | OH | OH | n-C3H7 |
| CH2CHCH2 | OH | OH | i-C3H7 |
| CH2CHCH2 | OH | OH | n-C4H9 |
| CH2CHCH2 | OH | OH | i-C4H9 |
| CH2CHCH2 | OH | OAc | C2H5 |
| PhCH2CH2 | OH | OH | CH3 |
| PhCH2CH2 | OH | OAc | CH3 |
| PhCH2CH2 | OH | OCH3 | CH3 |
| PhCH2CH2 | OAc | OH | CH3 |
| PhCH2CH2 | OAc | OAc | CH3 |
| PhCH2CH2 | OAc | OCH3 | CH3 |
| PhCH2CH2 | OCH3 | OH | CH3 |
| PhCH2CH2 | OCH3 | OAc | CH3 |
| PhCH2CH2 | OCH3 | OCH3 | CH3 |
| PhCH2CH2 | OH | OH | C2H5 |
| PhCH2CH2 | OH | OH | n-C3H7 |
| PhCH2CH2 | OH | OH | i-C3H7 |
| PhCH2CH2 | OH | OH | n-C4H9 |
| PhCH2CH2 | OH | OH | i-C4H9 |
| PhCH2CH2 | OH | OAc | C2H5 |

TABLE 2-continued

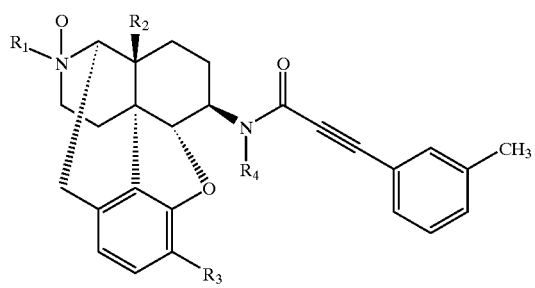

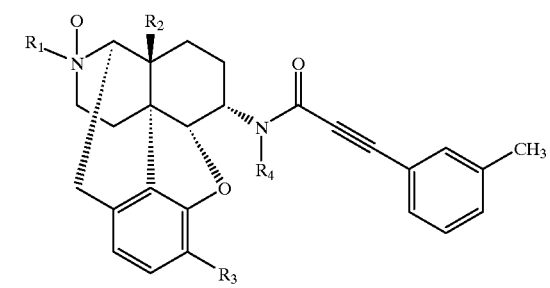

| R1 | R2 | R3 | R4 |
|---|---|---|---|
| C3H5CH2 | OH | OAc | CH3 |
| C3H5CH2 | OH | OCH3 | CH3 |
| C3H5CH2 | OH | H | CH3 |
| C3H5CH2 | OAc | OH | CH3 |
| C3H5CH2 | OAc | OAc | CH3 |
| C3H5CH2 | OAc | OCH3 | CH3 |
| C3H5CH2 | OAc | H | CH3 |
| C3H5CH2 | OCH3 | OH | CH3 |
| C3H5CH2 | OCH3 | OAc | CH3 |
| C3H5CH2 | OCH3 | OCH3 | CH3 |
| C3H5CH2 | OCH3 | H | CH3 |
| C3H5CH2 | OH | OAc | C2H5 |
| C3H5CH2 | OH | OAc | n-C3H7 |
| C3H5CH2 | OH | OAc | i-C3H5 |
| C3H5CH2 | OH | OCH3 | C2H5 |
| C3H5CH2 | OH | OCH3 | n-C3H7 |
| CH3 | OH | OH | CH3 |
| CH3 | OH | OAc | CH3 |
| CH3 | OH | OCH3 | CH3 |
| CH3 | OAc | OH | CH3 |
| CH3 | OAc | OAc | CH3 |
| CH3 | OAc | OCH3 | CH3 |
| CH3 | OCH3 | OH | CH3 |
| CH3 | OCH3 | OAc | CH3 |
| CH3 | OCH3 | OCH3 | CH3 |
| CH3 | OH | OH | C2H5 |
| CH3 | OH | OH | n-C3H7 |
| CH3 | OH | OH | i-C3H7 |
| CH3 | OH | OH | n-C4H9 |
| CH3 | OH | OH | i-C4H9 |
| CH3 | OH | OAc | C2H5 |
| CH2CHCH2 | OH | OH | CH3 |
| CH2CHCH2 | OH | OAc | CH3 |
| CH2CHCH2 | OH | OCH3 | CH3 |
| CH2CHCH2 | OAc | OH | CH3 |
| CH2CHCH2 | OAc | OAc | CH3 |
| CH2CHCH2 | OAc | OCH3 | CH3 |
| CH2CHCH2 | OCH3 | OH | CH3 |
| CH2CHCH2 | OCH3 | OAc | CH3 |
| CH2CHCH2 | OCH3 | OCH3 | CH3 |
| CH2CHCH2 | OH | OH | C2H5 |
| CH2CHCH2 | OH | OH | n-C3H7 |
| CH2CHCH2 | OH | OH | i-C3H7 |
| CH2CHCH2 | OH | OH | n-C4H9 |
| CH2CHCH2 | OH | OH | i-C4H9 |
| CH2CHCH2 | OH | OAc | C2H5 |
| PhCH2CH2 | OH | OH | CH3 |
| PhCH2CH2 | OH | OAc | CH3 |
| PhCH2CH2 | OH | OCH3 | CH3 |
| PhCH2CH2 | OAc | OH | CH3 |
| PhCH2CH2 | OAc | OAc | CH3 |
| PhCH2CH2 | OAc | OCH3 | CH3 |
| PhCH2CH2 | OCH3 | OH | CH3 |
| PhCH2CH2 | OCH3 | OAc | CH3 |
| PhCH2CH2 | OCH3 | OCH3 | CH3 |
| PhCH2CH2 | OH | OH | C2H5 |
| PhCH2CH2 | OH | OH | n-C3H7 |
| PhCH2CH2 | OH | OH | i-C3H7 |
| PhCH2CH2 | OH | OH | n-C4H9 |
| PhCH2CH2 | OH | OH | i-C4H9 |
| PhCH2CH2 | OH | OAc | C2H5 |

The compounds of this invention represented by general formula (III) can be obtained, to put it specifically, by the following method.

Generally, as shown by Chart 2, obtainment of the compounds can be achieved by the steps of oxidizing tertiary amine at 17 position of the starting material represented by general formula (IX) (where $R^1$, $R^2$, $R^3$, $R^4$, $R^5$ and A represent the same as defined in general formula (III)) with an organic peroxide such as m-chloroperbenzoic acid, performic acid, peracetic acid, perbenzoic acid, trifluoroperacetic acid, permaleic acid and perphthalic acid, but the oxidants should not be limited to them.

[Chart 2]

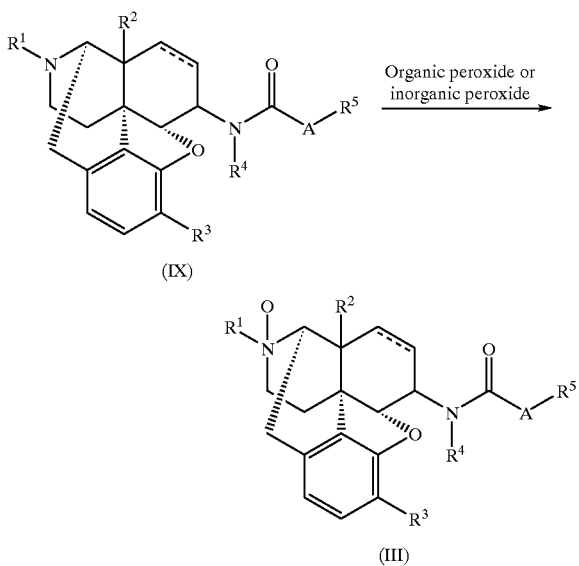

The starting material including tertiary amine at 17 position represented by general formula (VIII) can be produced by the method disclosed in Japanese Patent No. 2525552. There are many oxidizing agents that can be used for converting the starting material as represented by general formula (IX) into a tertiary amine N-oxide (III). m-chloroperbenzoic acid is convenient because generally it reacts comparatively rapidly to produce an N-oxide. However, other organic peroxides such as performic acid, peracetic acid, perbenzoic acid, trifluoroperacetic acid, permaleic acid and perphthalic acid may be used. Or alternatively, the oxidizing agent may be generated in the reaction system: a tertiary amine is dissolved in, for example, formic acid, acetic acid or trifluoroacetic acid, and aqueous hydrogen peroxide with a concentration of 3–50%, or more preferably with a concentration of 30–50% is added thereto. As a solvent, the halogen solvent such as methylene chloride, chloroform or 1,2-dichloroethane, the aromatic solvent such as benzene or toluene, the ether solvent such as diethylether or tetrahydrofuran, the alcohol solvent such as methanol, ethanol, propanol or tertiary buthanol may be used as the reaction medium. Or alternatively, when the oxidizing agent is generated in the reaction system, the corresponding acid may be used as the reaction medium as appropriate.

Instead of the organic peroxides described above, peroxides such as hydrogen peroxide may be used. Aqueous hydrogen peroxide alone may be used at a concentration of 3–50%, or it may be used in conjunction with a solvent like the one described above. Other usable oxidizing agents include ozone, tertiary butylhydroperoxide and cumene hydroperoxide.

Generally, the oxidizing agent may be used at 0° C. to the boiling point of solvent, or more specifically at room temperature to the boiling point of solvent, for several minutes to three days, or more specifically for one to 24 hours. The aforementioned oxidizing agent may be added by one equivalent with respect to one equivalent of tertiary amine, or it may be further added, for example, 10–100% excess or more excess to amine. When excess peroxide (which is easily detected by the use of iodine/starch paper) is present on completion of the reaction, addition of an inorganic reducing agent such as sodium bisulfite or sodium sulfite, a metal catalyst such as 5% platinum or palladium bound to carbon or alumina, or an organic reducing agent such as dimethylsulfide will ensure a proper treatment.

Other oxidizing agents to be used for the production of tertiary amine oxide include ozone in a solvent (for example, in chloroform, methylene chloride, fluorene or methanol), ozone adsorbed onto silica gel, hydroperoxide such as tertiary butylhydroperoxide, as desired, in the presence of a catalyst such as a vanadium compound.

When cost is important, for example, when the product is manufactured in an industrial scale, the preferable reaction agent is 30–50% aqueous hydrogen peroxide dissolved in tertiary buthanol. For example, when several kg of morphinan derivative (general formula (IX)) is allowed to react with 50% aqueous hydrogen peroxide dissolved in boiling tertiary buthanol for two and a half hours, it can be oxidized into a morphinan-N-oxide derivative (general formula (III)).

Further, of the compounds represented by general formula (IV) of the κ receptor agonist of this invention, preferred is trans-2-(3,4-dichlorophenyl)-N-methyl-N-[2-(1-pyrrolidinyl)cyclohexyl]acetamide; trans-N-methyl-N-[2-(1-pyrrolidinyl)cyclohexyl]benzo[b]thiophene-4-acetamide; (5β,7β,8α)-3,4-dichloro-N-methyl-N-[7-(1-pyrrolidinyl)-1-oxaspiro[4,5]dec-8-yl]benzeneacetamide; (5β,7β,8α)-N-methyl-N-[7-(1-pyrrolidinyl)-1-oxaspiro[4,5]dec-8-yl] benzo[b]furan-4-acetamide; or (5β,7β, 8α)-N-methyl-N-[7-(1-pyrrolidinyl)-1-oxaspiro[4,5]dec-8-yl] benzeneacetamide. The κ receptor agonists as represented by general formula (IV) can be produced according to the method disclosed by J. Szmuszkovicz et al., J. Med. Chem., 25, 1125(1982); D. C. Horwell et al., U.S. patent application Ser. No. 558737 (1983); J. Szmuszkovicz et al., Eur. Patent Appl. EP126612 (1984); and P. R. Halfpenny, D. C. Horwell et al., J. Med. Chem., 33, 286 (1990).

Of the compounds represented by general formula (V) of the κ receptor agonist of this invention, preferred is methyl 4-[(3,4-dichlorophenyl)acetyl]-3-[(1-pyrrolidinyl)methyl]-1-piperazinecarboxylate; 1-[(4-trifluoromethylphenyl) acetyl]-2-[(1-pyrrolidinyl)methyl]piperidine; or 1-[(3,4-dichlorophenyl)acetyl]-2-[(1-pyrrolidinyl)methyl] piperidine; 1-[(3,4-dichlorophenyl)acetyl]-4,4-ethylenedioxy-2-[(1-pyrrolidinyl)methyl]piperidine. The κ receptor agonists as represented by general formula (V) can be produced by the method provided by A. Naylor et al., J. Med. Chem., 36, 2075 (1993); V. Vecchietti et al., J. Med. Chem., 34, 397 (1991); ibid. Eur. Patent Appl. EP232, 612 (1987), EP260,041 (1988), EP275,696 (1988); D.I.C. Scopes et al., J. Med. Chem., 35, 490 (1992).

Of the compounds represented by general formula (VI) of the κ receptor agonists of this invention, 3-(1-pyrrolidinylmethyl)-4-[5,6-dichloro-1-indancarbonyl]-tetrahydro-1,4-thiazine is preferred. These κ receptor agonists represented by general formula (VI) can be produced by the method disclosed in WO 94/05646.

Of the compounds represented by general formula (VII) of the κ receptor agonists of this invention, 2-(3,4-dichlorophenyl)-N-methyl-N-[1-phenyl-2-(1-pyrrodinyl)ethyl]acetamide is preferred. These κ receptor agonists represented by general formula (VII) can be produced by the method disclosed by J. J. Barlow et al., J. Med. Chem., 34, 3149(1991).

In the production of said i receptor agonists, the pharmacologically acceptable, acid-supplementing salt to be added to the compounds represented by formulae (I), (III), (IV), (V), (VI) and (VII) may preferably include inorganic salts such as hydrochloric acid salts, sulfates, nitrates, hydrobromic acid salts, hydriodic acid salts, phosphates, etc.; organic carbonate such as acetates, lactates, succinates, oxalates, glutarates, malates, tartrates, fumarates, mandelates, maleates, benzoates, phthalates, etc.; and organic sulfonates such as methane sulfonates, ethane sulfonates, benzene sulfonates, p-toluene sulfonates, camphor sulfonates, etc. Of them, hydrochloric acid salts, hydrobromic acid salts, phosphates, tartrates, methane sulfonates and the like are preferred, but of course what is preferable is not limited to above.

These κ receptor agonists may be refined sufficiently pure to be used as a medicinal preparation, and, after having passed the necessary safety test, as the neat state or as a composition to be combined with a publicly known or pharmacologically accepted acid, vehicle, excipient or the like, can be administered orally or parenterally.

The oral preparation may occur as tablets and capsules, but, when used for the treatment of skin diseases, preferably may occur as topical preparations. Preparation of the topical preparations may comprise the steps of combining a fat (preferably, plant oil, animal oil, wax, fatty acid, fatty alcohol, mineral oil, turpentine oil, vaseline, etc.), a solvent (preferably, water, ethanol, glycerin, propylene glycol, isopropyl alcohol, ether, etc.), a preserving agent (preferably, paraoxybenzoic acid ester, benzoic acid, salicylic acid, sorbic acid, benzalkonium, benzethonium, propyleneglycol, chlorobuthanol, benzyl alcohol, ethanol, etc.), a stabilizer (preferably, tocopherol, butylhydroxyanisol, dibutylhydroxytoluene, sulfites, edetic acid disodium, etc.), an anionic surfactant (preferably, potassium soap, medical soap, zinc undecylenate, calcium stearate, magnesium stearate, aluminum monostearate, calcium linolate, sodium laurylsulfate, etc.), a non-ionic surfactant (preferably, glyceryl monostearate, sorbitan fatty acid partial esters, sugar fatty acid ester, stearic acid polyoxyl 40, macrogolic acids, lauromacrogol, polyoxyethylene160polyoxypropylene30glycol, polyoxyethylene hardened castor oil, polyoxyethylene sorbitan fatty acid partial esters, etc.), a cationic surfactant (preferably, benzalkonium chloride, benzethonium chloride, cetyl piridinium chloride, etc.), powders (preferably, zinc oxide, zinc powder in starch, kaolin, bismuth hyponitrite, titanium oxide, titanium dioxide, sulfur, anhydrous silicic acid, tarc, etc.), a preserving agent (preferably, paraoxybenzoic acid ester, sorbic acid, p-chloro-m-xylenol, Irgasan, hexachlorophene, etc.), an emulsifier (preferably, arabic gum powder, tragacanth powder, bentonite, carboxymethylcellulose sodium, methylcellulose, etc.), and a moisturizer (preferably, glycerin, propylene glycol, polyethylene glycol, 1,3-butylene glycol, sorbitol, polypyrrolidone carboxylic acid sodium, sodium lactate, sodium hyaluronate, chitin derivatives, urea, amino acids, sugar amino acid, etc.) to form a base, and of preparing it not only as an ointment, cream, emollient, lotion, patch, etc., but as a liquid preparation for topical use. Further, the preparation may be made as a solution for topical ophthalmic use.

The content of κ receptor agonist in a medicinal composition is not limited to any specific range, but the composition, to be used orally, should be prepared so that one ingestion may contain usually 0.1 µg–1000 mg, and, to be used topically, should be prepared so that one application may give a dose of usually 0.001 $ng/m^2$–10 $mg/m^2$.

EXAMPLES

This invention will be described below in concrete terms by means of Examples. However, the following Examples are given just for illustration, and this invention should not be limited to those Examples in any sense.

Example 1

17-cyclopropylmethyl-3,14β-dihydroxy-4,5α-epoxy-17-methyl-6β-(N-methyl-trans-3-(3-furyl)acrylamido)morphinanium idodide (1)

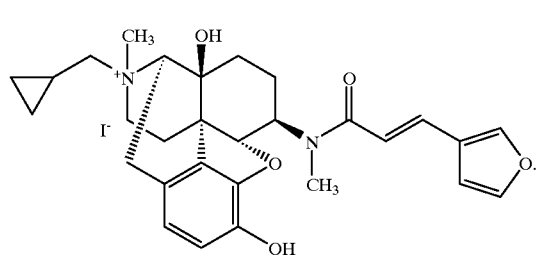

17-cyclopropylmethyl-3,14β-dihydroxy-4,5α-epoxy-6α-(N-methyl-trans-3-(3-furyl)acrylamido)morphinan 2.0699 g (4.3 mmol), ethyl acetate 60 ml, methanol 6 ml, and methyl iodide 1.3 ml were placed together in a container to be sealed, and, while being sealed, was stirred at 100° C. for four days. To the reaction solution was added methanol 60 ml; the precipitated solid was dissolved and concentrated; and to the resulting residue was added distilled water 400 ml. This aqueous solution was washed with chloroform (100 ml×7); the water phase was concentrated; the resulting residue was recrystallized from ethyl acetate-methanol; and the resulting crystal was dissolved in distilled water 500 ml. This aqueous solution was washed with chloroform (100 ml×3); the water phase was concentrated; the resulting residue was recrystallized three times from methanol; and the compound in the title 102 mg was obtained.

mp 202.40–207.9° C. (decomposition)

NMR(500 MHz, DMSO-d6) δ0.38(1H, m), 0.60(1H, m), 0.70(1H, m), 0.78(1H, m),1.23 (1.4H, m), 1.32 (0.6H, m), 1.40–1.62(2H,m), 1.73(1H, m), 1.97–2.22(1H, m), 2.63 (1H, m), 2.75(1H, m), 2.84–2.95(1H, m), 2.87(1.8H, s), 3.02–3.20(1H, m), 3.10(1.2H, s), 3.22–3.35(1H, m), 3.44–3.70(1.6H, m), 3.58(3H, s), 3.85 (2H, m), 4.18(0.4H, m), 4.80(0.6H, d, J=7.8 Hz), 4.88(0.4H, d, J=8.3 Hz), 5.86(0.4H, br s), 5.93(0.6H, br s), 6.36(0.6H, d, J=15.6 Hz), 6.63(0.6H, s), 6.71(1H, s), 6.77(0.4H, d, J=8.3 Hz), 6.84 (0.6H, d, J=7.8 Hz), 6.89 (0.4H, d, J=15.1 Hz), 6.99(0.4H, s), 7.23(0.6H, d, J=15.6 Hz), 7.36(0.4H, d, J=15.1 Hz), 7.66(0.6H, s), 7.72(0.4H, s), 7.92(0.6H, s), 8.03 (0.4H, s), 9.33(0.4H, s), 9.72(0.6H, s).

IR(KBr) ν3460, 1649, 1595, 1454, 1410, 1321, 1158, 1139, 596 $cm^{-1}$.

Mass(FAB) m/z 491$(M+H)^+$.

Elementary analysis $C_{29}H_{35}N_2O_5I_1 \cdot 0.5H_2O$: calculated values: C, 55.51; H, 5.78; N, 4.46; I, 20.22 measured values: C, 55.50; H, 5,86; N, 4.45; I, 20.23

Example 2

17-cyclopropylmethyl-3,14β-dihydroxy-4,5α-epoxy-17-methyl-6β-(N-methyl-3-methoxycinnamamido)morphinanium.iodide 2

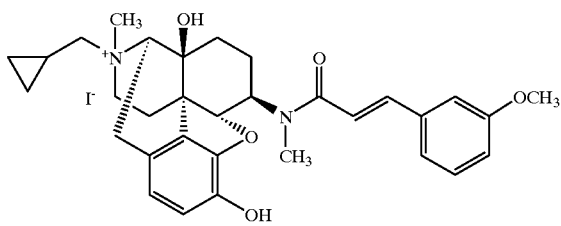

2

17-cyclopropylmethyl-3,14β-dihydroxy-4,5α-epoxy-6β-(N-methyl-3-methoxycinnamamido)morphinan 2.0014 g (3.9 mmol), tetrahydrofuran 40 ml, and methyl iodide 1.3 ml were placed together in a container to be sealed, and, while being sealed, was stirred at 100° C. for eight days. To the reaction solution was added methanol 60 ml; the precipitated solid was dissolved and concentrated; and the resulting residue was dissolved by a mixture 120 ml of chloroform and methanol; and extracted by distilled water 200 ml×3. The water phase was concentrated; and the resulting residue was recrystallized four times from methanol-distilled water, to give the compound 295 mg in the title.

mp: 176.0–183.0° C. (decomposition)

NMR(600 MHz, DMSO-d6) δ0.37(1H, m), 0.60(1H, m), 0.70(1H, m), 0.77(1H, m), 1.23(1.4H, m), 1.35(0.6H, m), 1.43–1.63(2H, m), 1.74(1H, m), 2.02–2.22(1H, m), 2.62(1H, m), 2.75(1H, m), 2.83–2.96(1H, m), 2.90(1.8H, s), 3.04–3.19(1H, m), 3.15(1.2H, s), 3.23–3.35(1H, m), 3.50 (0.6H, s), 3.53(0.4H, s), 3.59(3H, s), 3.68(0.6H, m), 3.78 (1.8H, s), 3.80(1.2H, s), 3.85(2H, m), 4.21(0.4H, m), 4.82 (0.6H, d, J=7.9 Hz), 4.89(0.4H, d, J=8.2 Hz), 5.87(0.4H, br s), 5.94 (0.6H, br s), 6.63(0.6H, d, J=15.0 Hz), 6.72(0.8H, s), 6.76(0.6H, d, J=8.2 Hz), 6.81(0.6H, d, J=8.2 Hz), 6.92(0.6H, dd, J=8.2 and 2.1 Hz), 6.96(0.4H, dd, J=8.2 and 2.1 Hz), 7.00(0.6H, m), 7.09(0.6H, d, J=7.6 Hz), 7.17(0.4H, d, J=15.3 Hz), 7.24–7.30(2H, m), 7.33(0.4H, t, J=7.9 Hz), 7.42(0.4H, d, J=15.3 Hz), 9.35(0.4H, s), 9.63(0.6H, s).

IR(KBr) ν3410, 1642, 1595, 1491, 1460, 1410, 1321, 1274, 857, 793 cm⁻¹.

Mass(FAB) m/z 531 (M+H)⁺.

Elementary analysis $C_{32}H_{39}N_2O_5.I_1.0.3H_2O$: calculated values: C, 57.89; H, 6.01; N, 4.22; I, 19.11 measured values: C, 57.80; H, 5,86; N, 4.22; I, 19.14

Example 3

17-cyclopropylmethyl-4,5α-epoxy-3,14β-dihydroxy-6β-[N-methyl-trans-3-(3-furyl)acrylamido]morphinan-N-oxide 3

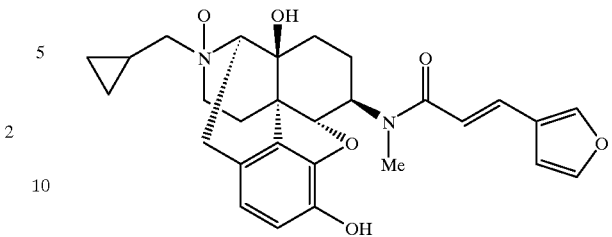

3

17-cyclopropylmethyl-4,5α-epoxy-3,14β-dihydroxy-6β-[N-methyl-trans-3-(3-furyl)acrylamido]morphinan 600 mg (1.26 mmol) was dissolved in tetrahydrofuran 30 ml; and to this solution was added dropwise at 0° C. for 15 minutes a solution which was obtained after m-chlorobenzoic acid 348 mg had been added to tetrahydrofuran 8 ml. On completion of the dropwise addition, the reaction solution was stirred at room temperature for about one hour and half, to which was added a mixture of chloroform/methanol (4:1), to dissolve precipitated solid in the reaction solution. The solution was concentrated; the resulting residue was purified by column chromatography [filled with alkaline alumina 20 g and chloroform/methanol (10:0 to 10:1)]; and the yield was recrystallized with ethyl acetate-methanol, to give the compound 473 mg (yield being 76%) in the title.

mp: 236–239.8° C. (decomposition)

NMR(600 MHz, CDCl₃) δ0.38(1H, m), 0.45(1H, m), 0.76(2H, m), 1.34(1H, m), 1.46(1H, m), 1.61(2H, m), 1.76 (1H, m), 2.25(0.2H, m), 2.42(0.8H, m), 2.90–3.03(1H, m), 3.05(2.4H, s), 3.06–3.22(4.6H, m), 3.41(2H, m), 3.72(0.8H, m), 3.79(1H, m), 4.58(0.2H, m), 4.67(0.8H, d, J=7.0 Hz), 4.75(0.2H, d, J=7.0 Hz), 6.35(0.8H, d, J=15.3 Hz), 6.59 (0.2H, d, J=8.2 Hz), 6.61(0.2H, d, J=15.3 Hz), 6.64(0.8H, d, J=8.2 Hz), 6.68(0.8H, s), 6.83(0.2H, d, J=8.2 Hz), 6.91(0.8 H, d, J=8.2 Hz), 7.32(0.8H, d, J=15.3 Hz), 7.33(1H, s), 7.38(0.8H, s), 7.43(0.2H, s), 7.55(0.2H, d, J=15.3 Hz), 7.62(0.2H, s), 9.49(1H, br s),12.12(1H, br s).

IR(KBr) ν3420, 1653, 1605, 1504, 1408, 1321, 1160, 872 cm⁻¹.

Mass(FAB) m/z 493 (M+H)⁺.

Elementary analysis $C_{28}H_{32}N_2O_6.0.2AcOEt$: calculated values: C, 67.80; H, 6.64; N, 5.49 measured values: C, 67.80; H, 6.67; N, 5.65

Example 4

17-cyclopropylmethyl-4,5α-epoxy-3,14β-dihydroxy-6β-(N-methyl-3-methoxycinnamamido) morphinan-N-oxide 4

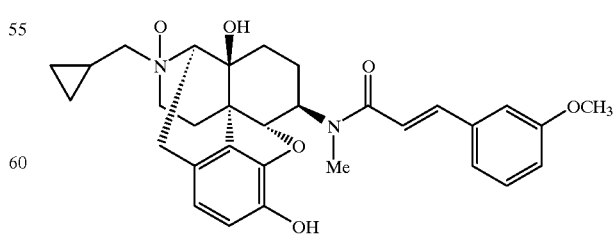

4

17-cyclopropylmethyl-4,5α-epoxy-3,14β-dihydroxy-6β-(N-methyl-3-methoxycinnamamido) morphinan 405 mg was dissolved in tetrahydrofuran 20 ml; and to this solution was added dropwise at 0° C. for ten minutes a solution which was obtained after m-chlorobenzoic acid 225 mg had been added to tetrahydrofuran 5 ml for dissolution. On completion of the dropwise addition, the reaction solution was stirred at room temperature for about 40 minutes; the reaction solution was concentrated; the residue was submitted to column chromatography based on the use of alkaline alumina 20 g; and the yield was recrystallized with ethyl acetate/methanol, to give the compound 329 mg (yield being 79%) in the title.

mp: 234–236.8° C. (decomposition)

NMR(600 MHz, $CDCl_3$) δ0.35(1H, m), 0.42(1H, m), 0.74(2H, m), 1.34(1H, m), 1.45(1H, m), 1. 61(2H, m), 1.72(1H, m), 1.81(2H, m), 2.24(0.3H, m), 2.41(0.7H, m), 2.86–2.97(1H, m), 2.97–3.14(2H, m), 3.06(2.1H, s), 3.15 (0.9H, s), 3.32–3.44 (2H, m), 3.70–3.80(1.7H, m), 3.83(3H, s), 4.62 (0.3H, m), 4.70(1H, d, J=7.9 Hz), 6.57–6.68(0.7H, m), 6.58(0.3H, d, J=7.9 Hz), 6.62(0.7H, d, J=8.2 Hz), 6.77(0.7H, dd, J=8.2 and 2.1 Hz), 6.82(0.3H, d, J=8.2 Hz), 6.84(0.7H, d, J=8.2 Hz), 6.86(1H, d, J=15.6 Hz), 6.91(0.3H, dd, J=8.2 and 2.1 Hz), 6.94(0.7H, d, J=7.3 Hz), 7.03(0.3H, s), 7.11(0.3H, d, J=7.6 Hz), 7.15(0.7H, t, J=7.9 Hz), 7.29 (0.3H, t, J=7.9 Hz), 7.40(0.7H, d, J=15.6 Hz), 7.62(0.3H, d, J=15.3 Hz), 9.00(1H, br s), 12.15(1H, br s).

IR(KBr) ν3420, 1647, 1593, 1495, 1408, 1321, 1160, 917, 855 $cm^{-1}$.

Mass(FAB) m/z 533 $(M+H)^+$.

Elementary analysis $C_{31}H_{36}N_2O_6 \cdot 0.3H_2O$: calculated values: C, 69.20; H, 6.86; N, 5.21 measured values: C, 68.11; H, 6.87; N, 5.21

Example 5

17-cyclopropylmethyl-4,5α-epoxy-3,14β-dihydroxy-6β-[N-methyl-3-(4-trifluoromethylphenyl)propyolamido]morphinan-N-oxide 5

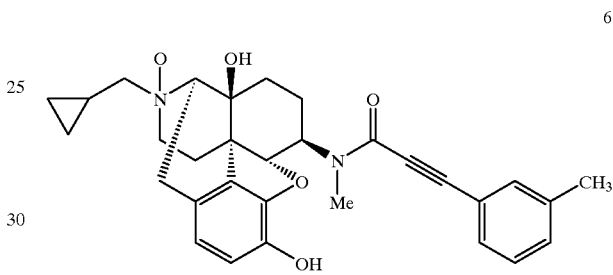

17-cyclopropylmethyl-4,5α-epoxy-3,14β-dihydroxy-6β-[N-methyl-3-(4-trifluoromethylphenyl)propyolamido]morphinan 413 mg was dissolved in tetrahydrofuran 20 ml; and to this solution was added dropwise at 0° C. for 15 minutes a solution which was obtained after m-chlorobenzoic acid 205 mg had been added to tetrahydrofuran 5 ml for dissolution. On completion of the dropwise addition, the reaction solution was stirred at room temperature for about one hour; the reaction solution was concentrated; the residue was submitted to column chromatography based on the use of alkaline alumina 20 g; and the yield was recrystallized with ethyl acetate/methanol, filtered and dried in a vacuum, to give the compound 304 mg (yield being 74%) in the title.

mp: 205–208° C. (decomposition)

NMR(600 MHz, $CDCl_3$) δ0.37(1H, m), 0.44(1H, m), 0.76(2H, m), 1.35(0.2H, m), 1.47(1.8H, m), 1.62(2H, m), 1.75(0.2H, m), 1.82(0.8H, m), 2.27(0.2H, m), 2.42(0.8H, m), 2.92(0.8H, m), 2.99(0.2H, m), 3.02–3.12(2H, m), 3.05 (2.4H, s), 3.12–3.22(2H, m), 3.31(0.6H, s), 3.40(2H, m), 3.79(1H, m), 4.22(0.8H, m), 4.50(0.2H, m), 4.74(0.8H, d, J=7.9 Hz), 4.76(0.2H, d, J=7.9 Hz), 6.00–7.20(1H, br s), 6.56–6.64(1.8H, m), 6.83(0.2H, d, J=7.9 Hz), 7.40(1.6H, d, J=7.9 Hz), 7.55(1.6H, d, J=8.2 Hz), 7.64(0.4H, d, J=8.5 Hz), 7.66(0.4H, d, J=8.5 Hz), 12.22(1H, br s).

IR(KBr) ν3420, 2224, 1615, 1506, 1408, 1325, 1170, 1129, 1067 $cm^{-1}$.

Mass(FAB) m/z 569 $(M+H)^+$.

Elementary analysis $C_{31}H_{31}N_2O_5F_3 \cdot 0.2C_6H_{12} \cdot 0.1AcOEt$: calculated values: C, 65.89; H, 5.80; N, 4.71; F, 9.59 measured values: C, 65.71; H, 5.86; N, 4.73; F, 9.52

Example 6

17-cyclopropylmethyl-4,5α-epoxy-3,14β-dihydroxy-6β-[N-methyl-3-(3-methylphenyl)propyolamido]morphinan-N-oxide 6

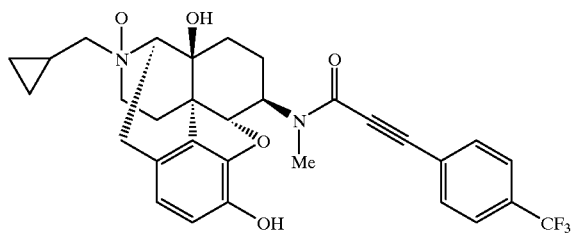

17-cyclopropylmethyl-4,5α-epoxy-3,14β-dihydroxy-6β-[N-methyl-3-(3-methylphenyl)propyolamido]morphinan 408 mg was dissolved in tetrahydrofuran 20 ml; and to this solution was added dropwise at 0° C. for 15 minutes a solution which was obtained after m-chlorobenzoic acid 244 mg had been added to tetrahydrofuran 5 ml for dissolution. On completion of the dropwise addition, the reaction solution was stirred at room temperature for about one hour; the reaction solution was concentrated; the residue was submitted to column chromatography based on the use of alkaline alumina 20 g; and the yield was recrystallized with ethyl acetate/methanol, filtered and dried in a vacuum, to give the compound 269 mg (yield being 64%) in the title.

mp: 192.0–202.0° C. (decomposition)

NMR(600 MHz, $CDCl_3$) δ0.37(1H, m), 0.44(1H, m), 0.75(2H, m), 1.35(0.3H, m), 1.40–1.53(1.7H, m), 1.54–1.66 (2H, m), 1.68–1.85(2H, m), 2.20–2.32(0.3H, m), 2.31(2.1H, s), 2.36(0.9H, s), 2.36–2.45(0.7H, m), 2.86–3.00(1H, m), 3.00–3.22 (3H, m), 3.03(2.1H, s), 3.31(0.9H, s), 3.34–3.46 (2H, m), 3.77(0.3H, m), 3.79(0.7H, m), 4.30(0.7H, m), 4.50(0.3H, m), 4.73(0.7H, d, J=8.2 Hz), 4.75(0.3H, d, J=8.5 Hz), 6.20–7.20(1H, br s), 6.59(0.3H, d, J=8.2 Hz), 6.60 (0.7H, d, J=8.2 Hz), 6.63(0.7H, d, J=8.2 Hz), 6.82(0.3H, d, J=8.2 Hz), 7.04(0.7H, s), 7.08(0.7H, d, J=6.1 Hz), 7.13–7.20 (1.4H, m), 7.23(0.3H, d, J=7.6 Hz), 7.26(0.3H, t, J=7.3 Hz), 7.35(0.3H, d, J=7.6 Hz), 7.37(0.3H, s), 12.22(1H, br s).

IR(KBr) ν3410, 2218, 1622, 1489, 1439, 1408, 1377, 1321, 1125, 1033, 915, 690 $cm^{-1}$.

Mass(FAB) m/z 515 $(M+H)^+$.

Elementary analysis $C_{31}H_{34}N_2O_5 \cdot 0.5H_2O$: calculated values: C, 71.11; H, 6.74; N, 5.35 measured values: C, 71.16; H, 6.73; N, 5.37

Example 7

Assay of opioid activity by Guinea pig ileum assay.

Male Hartley guinea pigs were used. The guinea pig was killed with a blow, and the ileum excised; the lumen of ileum was washed with a nutritious fluid; and only a piece of longitudinal muscle was stripped. This longitudinal muscle strip was suspended in a Magnus tube filled with Krebes-Henseleit solution (NaCl 135 mM; KCl 4.8 mM; $CaCl_2$ 3.4 mM; $KH_2PO_4$ 1.2 mM; $NaHCO_3$ 8.3 mM; $MgSO_4$, 2.5 mM; and glucose 11 mM) kept at 37° C., and gassed with a mixture of 5% carbon dioxide and 95% oxygen. Electrical stimulation was delivered at a rate of 0.1 Hz with 0.5 ms pulses through ring-shaped platinum electrodes placed at upper and lower levels in a Magnus tube. Tissue contractions were recorded via an isometric transducer on a polygraph.

The test drug was cumulatively added until it inhibited over 50% the contraction of specimen evoked by the electrical stimulation, in the presence or absence of naloxone as a μ antagonist, or nor-BNI as a κ antagonist, and IC50s were calculated for respective experimental conditions. From the difference in drug efficacy in the presence and absence of the antagonist, Ke values were calculated on the basis of following equations.

Ke=[Concentration of antagonist added]/(Dose ratio−1)

Dose ratio=$IC_{50}$ in the presence of antagonist/$IC_{50}$ in the absence of antagonist Compounds 1, 2, 3, 4, 5 and 6 were used as the test drug. When the ratio of Ke(μ) against Ke(κ) is calculated from the data shown in Table 3, Ke(μ)/Ke(κ) value ranges from 182 to ∞, which indicates that the compounds of this invention are agonists selectively acting on a κ receptor.

TABLE 3

Opioid activity of Compounds evaluated by guinea pig ileum assay

| | | Ke (nM) | |
|---|---|---|---|
| | IC50 (nM) | Naloxone (100 nM) | nor-BNI (5 nM) |
| 1 | 1.94 | 16.67 | 0.03 |
| 2 | 6.71 | 98.2 | 0.54 |
| 3 | 1.06 | — | 0.02 |
| 4 | 4.09 | 28.7 | 0.09 |
| 5 | 1.55 | 29.5 | 0.19 |
| 6 | 11.3 | 75.1 | 0.89 |

Example 8

Assay of opioid activity by mouse vas deferens assay

Male ddY mice were used for the experiment. The vas deferens specimen removed from the animal was suspended in a Magnus tube filled with Krebes-Henseleit solution (NaCl 120.7 nM; KCl 5.9 mM; $CaCl_2$ 2.5 mM; $NaH_2PO_4$ 1.2 mM; $NaHCO_3$ 15.5 mM; and glucose 11.5 mM) kept at 37° C., and gassed with a mixture of 5% carbon dioxide and 95% oxygen. Electrical stimulation was delivered at a rate of 0.1 Hz with 1.0 ms pulses through ring-shaped platinum electrodes placed at upper and lower levels in a Magnus tube. Tissue contractions were recorded via an isometric transducer on a polygraph.

The test drug was cumulatively added until it inhibited over 50% the contraction of specimen evoked by the electrical stimulation, in the presence or absence of naloxone as a μ antagonist, or nor-BNI as a κ antagonist, and $IC_{50}$s were calculated for respective experimental conditions. From the difference in drug efficacy in the presence and absence of the antagonist, Ke values were calculated on the basis of following equations.

Ke=[Concentration of antagonist added]/(Dose ratio−1)

Dose ratio=$IC_{50}$ in the presence of antagonist/$IC_{50}$ in the absence of antagonist Compounds 1, 2, 3, 4, 5 and 6 were used as the test drug. When the ratio of Ke(μ) against Ke(κ), and Ke(δ) against Ke(κ) values are calculated using the value listed on Table 4, Ke(μ)/Ke(κ) value ranges from 18 to ∞, and Ke(δ)/Ke(κ) does from 15 to ∞ respectively, which indicates that the compounds of this invention are agonists selectively acting on a κ receptor.

TABLE 4

Opioid activity of Compounds by mouse vas deferens assay

| | | Ke (nM) | | |
|---|---|---|---|---|
| | IC50 (nM) | Naloxone (30 nM) | NTI (10 nM) | nor-BNI (10 nM) |
| 1 | 4.42 | 14.18 | 11.23 | 0.17 |
| 2 | 5.9 | 100 | 25 | 0.45 |
| 3 | 2.14 | 30.48 | — | 0.040 |
| 4 | 1.80 | 50 | 11 | 0.67 |
| 5 | 0.59 | 5.9 | 5.0 | 0.33 |
| 6 | 4.6 | — | 20 | 0.26 |

Example 9

An opioid compound selectively acting on a κ receptor, (−)-17-(cyclopropylmethyl)-3,14β-dihydroxy-4,5α-epoxy-6β-[N-methyl-trans-3-(3-furyl)acrylamido]morphinan hydrochloride 7,

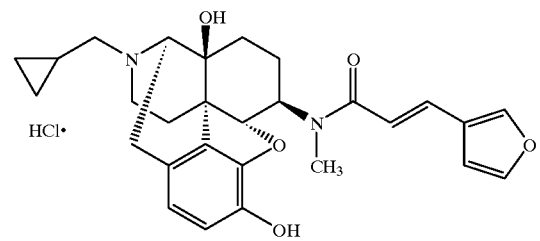

7 was dissolved in physiological saline, to give an aqueous solution with a concentration of 40 μg/ml. This aqueous solution was topically applied to three erupted lesions of urticaria, on the lower limb of a male adult at a dose of 0.2 μg/cm².

As a result, itching whose intensity was evaluated as moderate (ranked as "++") before treatment was completely eradicated five minutes after the treatment (ranked as "−"). No itching state continued for about five hours.

Example 10

An aqueous solution of Compound 7 was topically applied to the lesions on the skin surface of arm and leg of a female patient with atopic dermatitis which had caused severe itching (ranked as "+++").The drug solution was applied on five spots with a volume of about 50 μl per 10 cm², which was equivalent to a topical dose of 0.2 μg/cm². As a comparison, indomethacin cream (having a drug concentration of 7.5 mg/g) was applied at a dose of 75 μg/cm² in the same manner.

As shown in Table 5, the aqueous solution of Compound 7 eradicated itching completely from all the lesions to which it had been applied in five minutes after application. Thus it was confirmed that the compound 7 has a significant antipruritic activity. Further, no itching state continued at least three hours. On the other hand, the patient did not have complete relief from itching with treatment by indomethacin cream. Therefore, it was concluded that Compound 7 is more potent than indomethacin in terms of antipruritic activity in this condition.

TABLE 5

Antipruritic activities of a K receptor agonist (Compound 7) and indomethacin against itching due to atopic dermatitis

| Medicine used | Intensity of itching ("+++," maximum intensity, and "-," no itching) | | | |
|---|---|---|---|---|
| | Prior to application | 5 minutes after application | 10 minutes after application | 3 hours after application |
| Aqueous solution of Compound 7 | +++ | – | – | – |
| Indomethacin cream | +++ | +++ | + | ± |

Example 11

It was tested whether κ receptor agonists reduced the number of the scratching behavior induced by the subcutaneous administration of κ receptor antagonist, non-BNI, into the rostral back of ddY mice. To be noteworthy in this connection, it was confirmed that, when a buffer adjusted to pH 4–6 was administered subcutaneously into the rostral back of mice instead of nor-BNI, the administration itself did not induce any scratching behavior toward the treated skin in the mouse.

An opioid compound selectively active to a κ receptor, that is, trans-2-(3,4-dichlorophenyl)-N-methyl-N-[2-(1-pyrrolidinyl)cyclohexyl]acetamide (to be referred to as U-50488H) was dissolved in physiological saline. This aqueous solution was administered intraperitoneally to mice at a dose of 1, 3 or 10 mg/kg, and, 30 minutes after the administration, 0.1% solution of nor-BNI was subcutaneously administered into the skin of rostral back at a volume of 0.1 ml/10 g (body weight) to induce scratching. Following the nor-BNI administration, the number of scratching behavior was counted over 60 minutes.

In another session, chlorophenylamine, an anti-histamine agent was dissolved in physiological saline, and this solution was administered intraperitoneally to mice at a dose of 0.3, 1.0 or 3.0 mg/kg. Thirty minutes after the administration, nor-BNI was administered and the number of scratching behavior was counted as mentioned before. In a third session, to provide a control, a saline-treated group was implemented for which, following nor-BNI administration, the number of scratching behavior was counted over 60 minutes. The above sessions of experiment were performed on groups each of which comprises 10 animals.

As shown in FIG. 1, in the saline-treated group, a significant increase in the numbers of scratching behavior were observed as a result of nor-BNI administration, while, in the U-50488H treated group, the number of scratching behavior induced by nor-BNI treatment decreased significantly. This result suggests that the test substance has a significant antipruritic activity. On the other hand, in the chlorophenylamine-treated group, the number of scratching behavior was decreased, but the degree of it was less than that of U-50488H. These results indicate that, as far as antipruritic activity is concerned, U-50488H is more potent than chlorophenylamine.

Example 12

Male ddY mice were purchased from Japan SLC when they were 4 weeks old, and used in the experiments when they became 5 weeks old after acclimation. The day before experiment, the mouse had hair on the rostral back skin clipped with a hair clipper. Each of test drug was dissolved in 10% DMSO. Either of the test drug or solvent was administered subcutaneously into rostral back of the mouse, and 30 minutes later Compound 48/80 dissolved in saline was administered intradermally into the hair-clipped skin at a dose of about 50 μl (100 μg/site). Immediately thereafter, the mouse was put into a cage for observation (10×7×16 cm), and the subsequent behavior of the mouse was recorded with a video camera under unmanned conditions. The video tape was replayed, and the number of the scratching of the Compound 48/80-treated site or its vicinity by hind paws was counted. Each experimental group comprised 8 to 10 animals.

Inhibition percent of scratching by the test compound was calculated by averaging the inhibition of scratching behavior (%) of each mice, which is obtained on the basis of the following equation. The degree of inhibition was regarded as correlated with antipruritic potential of the test compound.

Inhibition of scratching behavior (%)=[1−(A−C/B−C)]×100

A=Scratching count of each mouse which received a test drug
B=Scratching count of each mouse which received solvent instead of a test drug
C=Scratching count of each mouse which received solvent instead of the pruritic agent The test compounds used included 17-cyclopropylmethyl-3,14β-dihydroxy-4,5α-epoxy-17-methyl-6β-(N-methyl-3-methoxycinnamamido) morphinanium iodide 2; 17-cyclopropylmethyl-3,14β-dihydroxy-4,5α-epoxy-6β-[N-methyl-trans-3-(3-furyl) acrylamido]morphinan-N-oxide 3; 17-cyclopropylmethyl-3, 14β-dihydroxy-4,5α-epoxy-6β-[N-methyl-3-(4-trfluoromethylphenyl)propyolamido]morphinan-N-oxide 5; 17-cyclopropylmethyl-3,14β-dihydroxy-4,5α-epoxy-6β-[N-methyl-3-(3-methylphenyl)propyolamido]morphinan-N-oxide 6; 17-cyclopropylmethyl-3,14β-dihydroxy-4,5α-epoxy-6β-[N-methyl-trans-3-(3-furyl)acrylamido] morphinan hydrochloride 7: 17-cyclopropylmethyl-3,14β-dihydroxy-4,5α-epoxy-6β-(N-methyl-3-methoxycinnamamido]morphinan tartrate 8; 17-cyclopropylmethyl-3,14β-dihydroxy-4,5α-epoxy-6β-[N-(1,4-dioxo-4-methoxy-trans-2-butenyl)-N-methyl] morphinan methanesulfonate 9; 17-cyclopropylmethyl-3, 14β-dihydroxy-4,5α-epoxy-6β-(N-methyl-3,4-dichlorophenylacetamido]morphinan hydrochloride 10; 17-cyclopropylmethyl-3,14β-dihydroxy-4,5α-epoxy-6β-(N-methylcinnamamido)morphinan hydrochloride 11; 17-cyclopropylmethyl-3,14β-dihydroxy-4,5α-epoxy-6β-(N-methyl-N'-benzylureido)morphinan tartrate 12; 17-cyclopropylmethyl-3,14β-dihydroxy-4,5α-epoxy-6β-(N-methylbenzyloxycarbamido)morphinan hydrochloride 13; 17-cyclopropylmethyl-3,14β-dihydroxy-4,5α-epoxy-6β-(benzyloxycarbamido)morphinan hydrochloride 14; 17-cyclopropylmethyl-3,14β-dihydroxy-4,5α-epoxy-6α-(N-methylphenylmethanesulfonamido)morphinan hydrochloride 15; 17-(cyclopropylmethyl)-3,14β-dihydroxy-4,5α-epoxy-6β-[N-methyl-trans-3-(4-bromo-2-thiofuryl)acrylamido]morphinan hydrobromide 16; 17-cyclopropylmethyl-3,14β-dihydroxy-4,5α-epoxy-6β-[N-methyl-3-(phenyl)propyolamido]morphinan hydrochloride 17; 17-cyclopropylmethyl-3,14β-dihydroxy-4,5α-epoxy-6β-[N-methyl-3-(3-methylphenyl)propyolamido]morphinan hydrochloride 18; 17-cyclopropylmethyl-3,14β-dihydroxy-4,5α-epoxy-6β-[N-methyl-3-(4-trifluoromethylphenyl)propyolamido]morphinan hydrochloride 19: 2-(3,4-dichlorophenyl)-N-methyl-N-[1-phenyl-2-(1-pyrrolidinyl)ethyl]acetamide hydrochloride 20; 3-(1-pyrrolidinylmethyl)-4-[5,6-dichloro-1-indancarbonyl]-tetrahydro-1,4-thiazine hydrochloride 21; trans-N-methyl-N-[2-(1-pyrrolidinyl)cyclohexyl]benzo [b]thiophene-4-acetaminde hydrochloride 22; and (5β, 7β, 8α)-N-methyl-N-[7-(1-pyrrolidinyl)-1-oxaspiro [4,5]dec-8-yl]benzo[b]furan-4-acetamide hydrochloride 23.

12

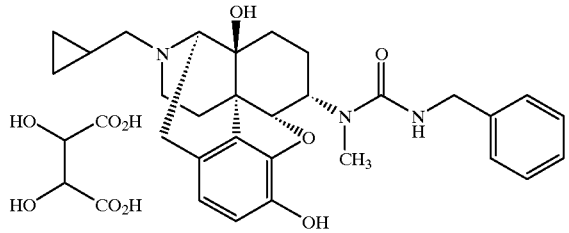

13

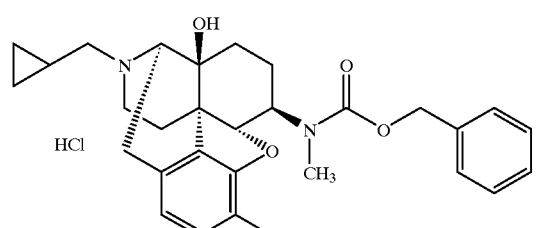

14

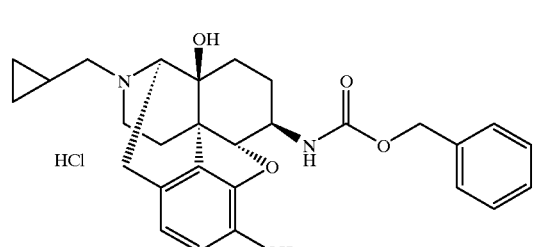

8

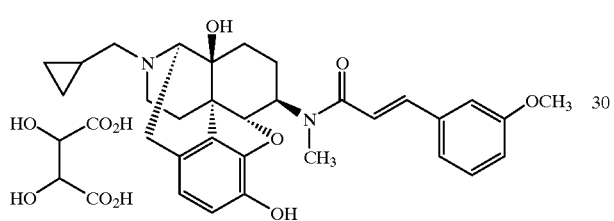

9

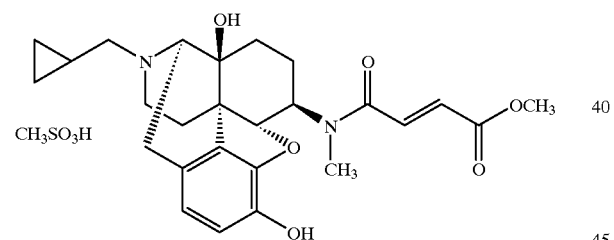

15

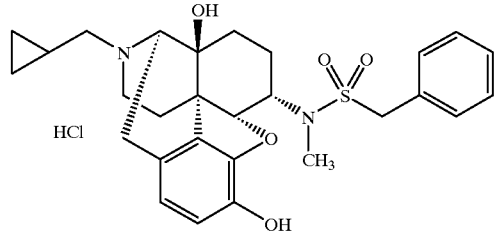

10

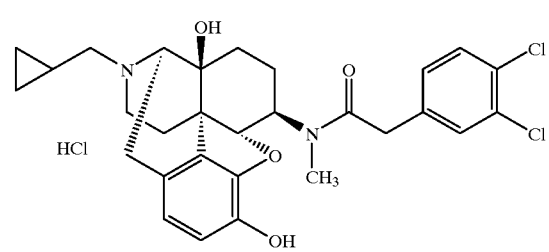

16

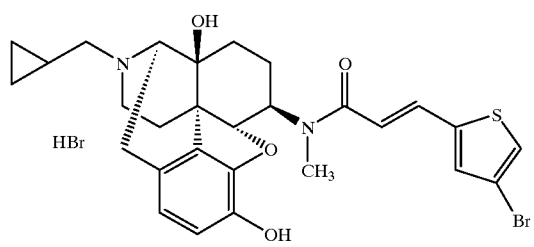

11

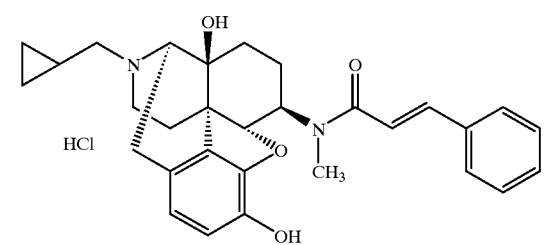

17

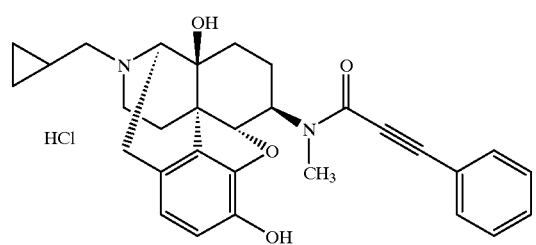

18

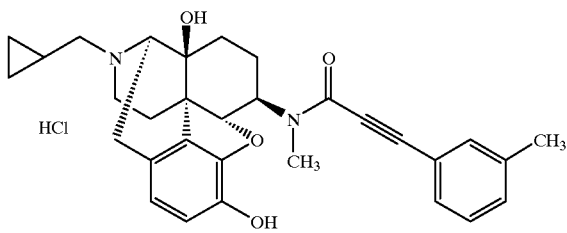

19

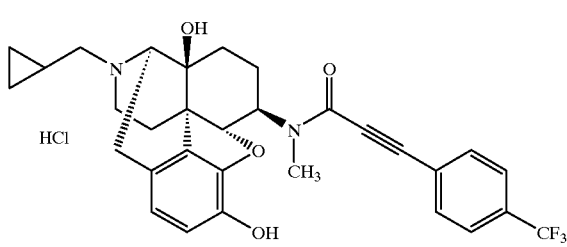

20

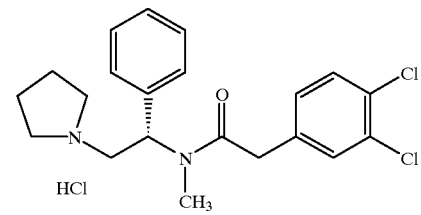

21

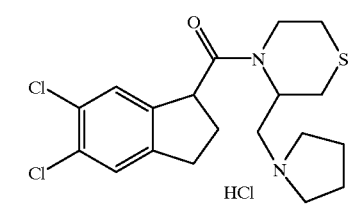

22

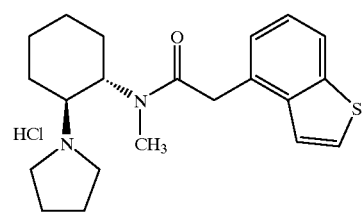

23

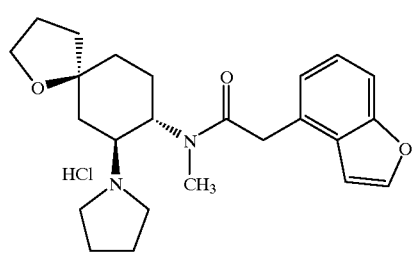

The results are summarized in Table 6. The compounds used for the test exhibited an antipruritic activity at the dose used.

TABLE 6

Antipruritic activities of various opioid K receptor agonists

| Test preparation | Dose (mg/kg) | Inhibition (%) |
| --- | --- | --- |
| Compound 2 | 1.0 | 41 |
| Compound 3 | 0.0057 | 64 |
| Compound 5 | 0.016 | 55 |
| Compound 6 | 0.005 | 45 |
| Compound 7 | 0.005 | 58 |
| Compound 8 | 0.01 | 72 |
| Compound 9 | 1.8 | 52 |
| Compound 10 | 0.46 | 14 |
| Compound 11 | 0.0018 | 45 |
| Compound 12 | 0.07 | 39 |
| Compound 13 | 0.07 | 47 |
| Compound 14 | 0.31 | 46 |
| Compound 15 | 1.88 | 56 |
| Compound 16 | 0.0046 | 14 |
| Compound 17 | 0.0066 | 90 |
| Compound 18 | 0.03 | 92 |
| Compound 19 | 0.03 | 40 |
| Compound 20 | 0.006 | 62 |
| Compound 21 | 0.0003 | 23 |
| Compound 22 | 1.2 | 70 |
| Compound 23 | 0.0069 | 46 |

Industrial Applicability

An antipruritic of this invention comprises an opiate κ receptor agonist as an effective component, and is useful for dermatoses with pruritus such as atopic dermatitis, nervous dermatitis, contact dermatitis, seborrheic dermatitis, autosensitization dermatitis, caterpillar dermatitis, asteatosis, senile pruritus cutaneous, insect sting, photosensitive dermatosis, urticaria, prurigo, herpes, impetigo, eczema, tinea, lichen, psoriasis, scabies, and acne vulgaris; visceral diseases complicated with pruritus such as malignant tumors, diabetes mellitus, hepatic diseases, renal failure, hemodialysis, and pregnancy.

What is claimed is:

1. A method for treating pruritus in a mammalian patient comprising administering a therapeutically effective amount of opiate K receptor agonist wherein the opiate K receptor agonist is a morphinan quaternary ammonium salt derivative represented by the general formula (II):

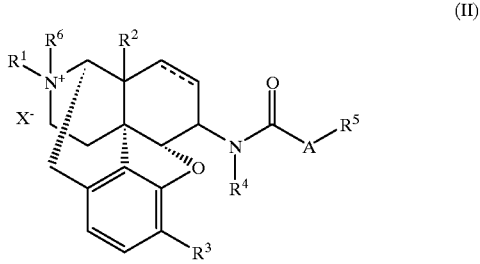

(II)

wherein === is a double bond, or a single bond; $R^1$ is alkyl having 1 to 5 carbon atoms, cycloalkylalkyl having 4 to 7 carbon atoms, cycloalkenylalkyl having 5 to 7 carbon atoms, aralkyl having 7 to 13 carbon atoms, alkenyl having 4 to 7 carbon atoms, or allyl; $R^2$ is hydrogen, hydroxy, nitro, alkanoyloxy having 1 to 5 carbon atoms; $R^3$ is hydrogen, hydroxy, alkanoyloxy having 1 to 5 carbon atoms, or alkoxy having 1 to 5 carbon atoms; $R^4$ is hydrogen, a straight or branched alkyl having 1 to 5 carbon atoms, or aryl having 6 to 12 carbon atoms; A is alkylene having 1 to 6 carbon atoms, —CH=CH—, or —C≡C—; and $R^5$ is an organic group having any one of the following fundamental structures:

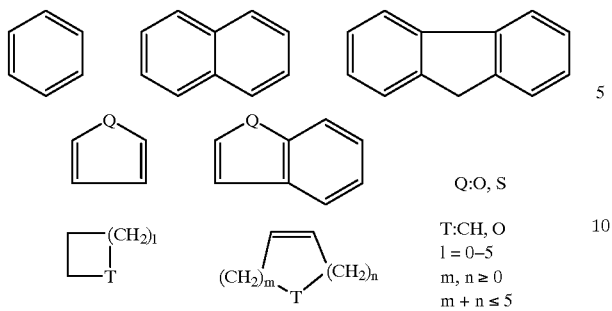

Q:O, S
T:CH, O
l = 0–5
m, n ≥ 0
m + n ≤ 5 wherein the organic group may have at least one substituent selected from the group consisting of alkyl having 1 to 5 carbon atoms, alkoxy having 1 to 5 carbon atoms, alkanoyloxy having 1 to 5 carbon atoms, hydroxy, fluorine, chlorine, bromine, iodine, nitro, cyano, isothiocyanato, trifluoromethyl, trifluoromethoxy and methylenedioxy; $R^6$ is alkyl having 1 to 5 carbon atoms, or allyl; $X^-$ denotes an anion to form a pharmacologically acceptable salt; and the general formula (II) comprises (+), (−), and (±) isomers.

2. A method for treating pruritus according to claim 1, wherein the morphinan quaternary ammonium salt derivative is represented by the general formula (II), wherein $R^1$ is methyl, ethyl, propyl, butyl, isobutyl, cyclopropylmethyl, allyl, benzyl, or phenethyl; $R^2$ and $R^3$ are hydrogen, hydroxy, acetoxy, or methoxy independently; $R^4$ is hydrogen, or a straight or branched alkyl having 1 to 5 carbon atoms; A is —CH=CH— or —C≡C—; and $R^6$ is methyl.

3. A method for treating pruritis according to claim 2, wherein the morphinan quaternary ammonium salt derivative is represented by the general formula (II), wherein $R^4$ is methyl, ethyl, propyl, isopropyl, butyl, or isobutyl.

4. A method for treating pruritis according to claim 2, wherein the morphinan quaternary ammonium salt derivative is represented by the general formula (II), wherein $R^5$ is an organic group having any one of the following fundamental structures:

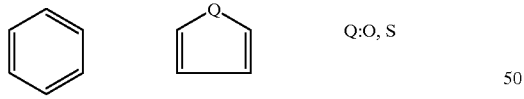

Q:O, S wherein the organic group may have at least one substituent selected from the group consisting of alkyl having 1 to 5 carbon atoms, alkoxy having 1 to 5 carbon atoms, alkanoyloxy having 1 to 5 carbon atoms, hydroxy, fluorine, chlorine, bromine, iodine, nitro, cyano, isothiocyanato, trifluoromethyl, trifluoromethoxy, and methylenedioxy.

5. A method for treating pruritis according to claim 4, wherein the morphinan quaternary ammonium salt derivative is represented by the general formula (II), wherein $R^4$ is methyl, ethyl, propyl, isopropyl, butyl, or isobutyl.

6. A method for treating pruritis according to claim 1, wherein pruritus is a complication of dermatosis or visceral disease.

7. An antipruritic pharmaceutical composition comprising a therapeutically effective amount of opiate K receptor agonist wherein the opiate K receptor agonist is a morphinan quaternary ammonium salt derivative represented by the general formula (II):

(II)

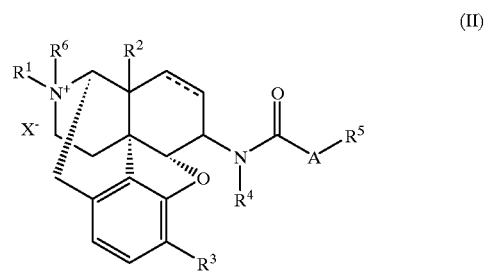

wherein ═══ is a double bond, or a single bond; $R^1$ is alkyl having 1 to 5 carbon atoms, cycloalkylalkyl having 4 to 7 carbon atoms, cycloalkenylalkyl having 5 to 7 carbon atoms, aralkyl having 7 to 13 carbon atoms, alkenyl having 4 to 7 carbon atoms, or allyl; $R^2$ is hydrogen, hydroxy, nitro, alkanoyloxy having 1 to 5 carbon atoms; $R^3$ is hydrogen, hydroxy, alkanoyloxy having 1 to 5 carbon atoms, or alkoxy having 1 to 5 carbon atoms; $R^4$ is hydrogen, a straight or branched alkyl having 1 to 5 carbon atoms, or aryl having 6 to 12 carbon atoms; A is alkylene having 1 to 6 carbon atoms, —CH=CH—, or —C≡C—; and $R^5$ is an organic group having any one of the following fundamental structures:

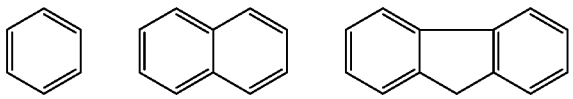

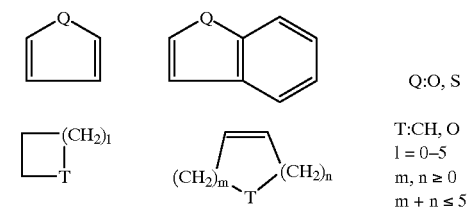

Q:O, S
T:CH, O
l = 0–5
m, n ≥ 0
m + n ≤ 5 wherein the organic group may have at least one substituent selected from the group consisting of alkyl having 1 to 5 carbon atoms, alkoxy having 1 to 5 carbon atoms, alkanoyloxy having 1 to 5 carbon atoms, hydroxy, fluorine, chlorine, bromine, iodine, nitro, cyano, isothiocyanato, trifluoromethyl, trifluoromethoxy and methylenedioxy; $R^6$ is alkyl having 1 to 5 carbon atoms, or allyl; $X^-$ denotes an anion to form a pharmacologically acceptable salt; and the general formula (II) comprises (+), (−), and (±) isomers; and wherein said composition is in the form of a topical application.

8. A morphinan quaternary ammonium salt derivative represented by the general formula (II):

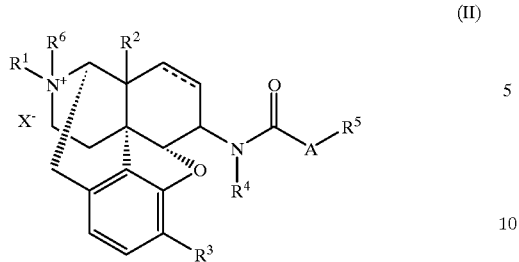

(II)

wherein === is a double bond, or a single bond; $R^1$ is alkyl having 1 to 5 carbon atoms, cycloalkylalkyl having 4 to 7 carbon atoms, cycloalkenylalkyl having 5 to 7 carbon atoms, aralkyl having 7 to 13 carbon atoms, alkenyl having 4 to 7 carbon atoms or allyl; $R^2$ is hydrogen, hydroxy, nitro, alkanoyloxy having 1 to 5 carbon atoms, alkoxy having 1 to 5 carbon atoms, or alkyl having 1 to 5 carbon atoms; $R^3$ is hydrogen, hydroxy, alkanoyloxy having 1 to 5 carbon atoms, or alkoxy having 1 to 5 carbon atoms; $R^4$ is hydrogen, a straight or branched alkyl having 1 to 5 carbon atoms, or aryl having 6 to 12 carbon atoms; A is alkylene having 1 to 6 carbon atoms, —CH=CH—, or —C≡C—; and $R^5$ is an organic group having any one of the following fundamental structures:

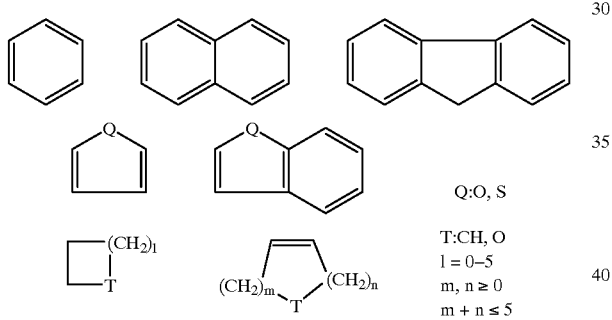

T:CH, O
l = 0–5
m, n ≥ 0
m + n ≤ 5 wherein the organic group may have at least one substituent selected from the group consisting of alkyl having 1 to 5 carbon atoms, alkoxy having 1 to 5 carbon atoms, alkanoyloxy having 1 to 5 carbon atoms, hydroxy, fluorine, chlorine, bromine, iodine, nitro, cyano, isothiocyanato, trifluoromethyl, trifluoromethoxy, and methylenedioxy; $R^6$ is alkyl having 1 to 5 carbon atoms, or allyl; $X^-$ denotes an anion to form a pharmacologically acceptable salt; and the general formula (II) comprises (+), (-), and (±) isomers.

9. A morphinan quaternary ammonium salt derivative according to claim 8, wherein $R^1$ is methyl, ethyl, propyl, butyl, isobutyl, cyclopropylmethyl, allyl, benzyl, or phenethyl; $R^2$ and $R^3$ are hydrogen, hydroxy, acetoxy, or methoxy independently; $R^4$ is hydrogen, or a straight or branched alkyl having 1 to 5 carbon atoms; A is —CH=CH— or —C≡C—; and $R^6$ is methyl.

10. A morphinan quaternary ammonium salt derivative according to claim 9, wherein $R^4$ is methyl, ethyl, propyl, isopropyl, butyl, or isobutyl.

11. A morphinan quaternary ammonium salt derivative according to claim 9 represented by the general formula (II), wherein $R^5$ is an organic group having any one of the following fundamental structures:

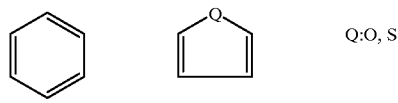

wherein the organic group may have at least one substituent selected from the group consisting of alkyl having 1 to 5 carbon atoms, alkoxy having 1 to 5 carbon atoms, alkanoyloxy having 1 to 5 carbon atoms, hydroxy, fluorine, chlorine, bromine, iodine, nitro, cyano, isothiocyanato, trifluoromethyl, trifluoromethoxy, and methylenedioxy.

12. A morphinan quaternary ammonium salt derivative according to claim 11 represented by the general formula (II), wherein $R^4$ is methyl, ethyl, propyl, isopropyl, butyl, or isobutyl.

13. A pharmaceutical composition comprising a morphinan quaternary ammonium salt derivative according to any one of claims 8 to 12.

14. A method for preparing a compound represented by the general formula (II) wherein a tertiary amine represented by the general formula (VIII) is quaternized with an alkylating agent:

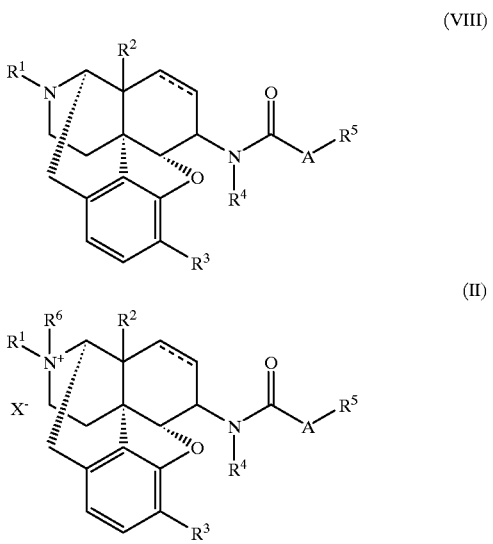

wherein in the above general formulas (VIII) and (II), === is a double bond, or a single bond; $R^1$ is alkyl having 1 to 5 carbon atoms, cycloalkylalkyl having 4 to 7 carbon atoms, cycloalkenylalkyl having 5 to 7 carbon atoms, aralkyl having 7 to 13 carbon atoms, alkenyl having 4 to 7 carbon atoms, or allyl; $R^2$ is hydrogen, hydroxy, nitro, alkanoyloxy having 1 to 5 carbon atoms, alkoxy having 1 to 5 carbon atoms or alkyl having 1 to 5 carbon atoms; $R^3$ is hydrogen, hydroxy, alkanoyloxy having 1 to 5 carbon atoms, or alkoxy having 1 to 5 carbon atoms; $R^4$ is hydrogen, a straight or branched alkyl having 1 to 5 carbon atoms, or aryl having 6 to 12 carbon atoms; A is alkylene having 1 to 6 carbon atoms, —CH=CH—, or —C≡C—; and $R^5$ is an organic group having any one of the following fundamental structures:

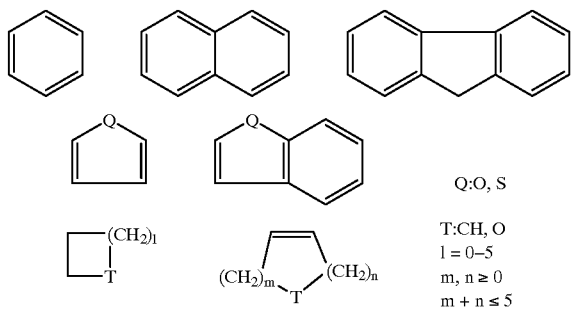

wherein the organic group may have at least one substituent selected from the group consisting of alkyl having 1 to 5 carbon atoms, alkoxy having 1 to 5 carbon atoms, alkanoyloxy having 1 to 5 carbon atoms, hydroxy, fluorine, chlorine, bromine, iodine, nitro, cyano, isothiocyanato, trifluoromethyl, trifluoromethoxy, and methylenedioxy.

15. A method according t o claim 14, wherein the alkylating agent is alkyl iodide having 1 to 5 carbon atoms, alkyl bromide having 1 to 5 carbon atoms, alkyl chloride having 1 to 5 carbon atoms, alkyl methanesulfonate having 1 to 5 carbon atoms, dialkyl sulfate having 1 to 5 carbon atoms, allyl iodide, allyl bromide, or allyl chloride.

* * * * *

UNITED STATES PATENT AND TRADEMARK OFFICE
CERTIFICATE OF CORRECTION

PATENT NO.   : 6,316,461 B1
DATED        : November 13, 2001
INVENTOR(S)  : Nagase et al.

It is certified that error appears in the above-identified patent and that said Letters Patent is hereby corrected as shown below:

Title page,
Item [57], change the "ABSTRACT" to read
-- An antipruritic pharmaceutical composition having an opiate K receptor agonist as an effective component; a new morphinan quaternary ammonium salt derivative and a new morphinan-N-oxide derivative which are useful in treating pruritus associated with some diseases; and a method for treating pruritus by administering an antipruritic pharmaceutical composition having an opiate K receptor as an effective component. --

Column 6,
Line 41, before ";" delete "13" and please insert -- - --

Column 13,
Table 1 continued after Row "S", "CH3", "H", "H" please insert the following:

| | | | | |
|---|---|---|---|---|
| -- | S | H | CF3 | H |
| | S | H | H | CF3 |
| | S | CN | H | H |
| | S | H | CN | H |
| | S | H | H | CN |
| · | C3H5CH2 | OH | OAc | CH3 |
| | C3H5CH2 | OH | OCH3 | CH3 |
| | C3H5CH2 | OH | H | CH3 |
| | C3H5CH2 | OAc | OH | CH3 |
| | C3H5CH2 | OAc | OAc | CH3 |
| | C3H5CH2 | OAc | OCH3 | CH3 |

UNITED STATES PATENT AND TRADEMARK OFFICE
CERTIFICATE OF CORRECTION

PATENT NO. : 6,316,461 B1
DATED : November 13, 2001
INVENTOR(S) : Nagase et al.

It is certified that error appears in the above-identified patent and that said Letters Patent is hereby corrected as shown below:

Column 13 cont'd.

| | | | | |
|---|---|---|---|---|
| C3H5CH2 | OAc | H | CH3 | |
| C3H5CH2 | OCH3 | OH | CH3 | |
| C3H5CH2 | OCH3 | OAc | CH3 | |
| C3H5CH2 | OCH3 | OCH3 | CH3 | |
| C3H5CH2 | OCH3 | H | CH3 | |
| C3H5CH2 | OH | OH | C2H5 | -- |

Column 14,
After Row "PhCH2CH2" "OH", "OH", "n-C3H7" please insert the following:

| | | | | |
|---|---|---|---|---|
| -- | PhCH2CH2 | OH | OH | i-C3H7 |
| | PhCH2CH2 | OH | OH | n-C4H9 |
| | PhCH2CH2 | OH | OH | i-C4H9 |
| | PhCH2CH2 | OH | OAc | C2H5 |

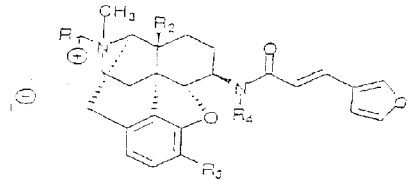

| | | | |
|---|---|---|---|
| C3H5CH2 | OH | OAc | CH3 |
| C3H5CH2 | OH | OCH3 | CH3 |
| C3H5CH2 | OH | H | CH3 |
| C3H5CH2 | OAc | OH | CH3 |
| C3H5CH2 | OAc | OAC | CH3 |
| C3H5CH2 | OAc | OCH3 | CH3 |
| C3H5CH2 | OAc | H | CH3 |
| C3H5CH2 | OCH3 | OH | CH3 |
| C3H5CH2 | OCH3 | OAc | CH3 |
| C3H5CH2 | OCH3 | OCH3 | CH3 |

UNITED STATES PATENT AND TRADEMARK OFFICE
CERTIFICATE OF CORRECTION

PATENT NO. : 6,316,461 B1
DATED : November 13, 2001
INVENTOR(S) : Nagase et al.

It is certified that error appears in the above-identified patent and that said Letters Patent is hereby corrected as shown below:

Column 14 cont'd.

| C3H5CH2 | OCH3 | H  | CH3    |    |
|---------|------|----|--------|----|
| C3H5CH2 | OH   | OH | C2H5   |    |
| C3H5CH2 | OH   | OH | n-C3H7 |    |
| C3H5CH2 | OH   | OH | i-C3H7 |    |
| C3H5CH2 | OH   | OH | n-C4H9 | -- |

Column 41,
Line 8, after "said" please change "i" to -- K --

Column 42,
Line 18, after "morphinanium" please change "idodide" to -- iodide --

Column 44,
Line 29, after "mp:" please change "236" to -- 238 --

Column 49,
Line 36, please change "ddY" to -- DDY --

Signed and Sealed this

Tenth Day of September, 2002

Attest:

Attesting Officer

JAMES E. ROGAN
*Director of the United States Patent and Trademark Office*